US011918176B2

United States Patent
Oosake et al.

(10) Patent No.: US 11,918,176 B2
(45) Date of Patent: Mar. 5, 2024

(54) MEDICAL IMAGE PROCESSING APPARATUS, PROCESSOR DEVICE, ENDOSCOPE SYSTEM, MEDICAL IMAGE PROCESSING METHOD, AND PROGRAM

(71) Applicant: FUJIFILM Corporation, Tokyo (JP)

(72) Inventors: Masaaki Oosake, Kanagawa (JP); Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 282 days.

(21) Appl. No.: 17/391,644

(22) Filed: Aug. 2, 2021

(65) Prior Publication Data

US 2021/0366110 A1 Nov. 25, 2021

Related U.S. Application Data

(63) Continuation of application No. PCT/JP2019/040362, filed on Oct. 15, 2019.

(30) Foreign Application Priority Data

Mar. 8, 2019 (JP) .................................. 2019-042741

(51) Int. Cl.
*A61B 1/00* (2006.01)
*G06F 18/2431* (2023.01)
(Continued)

(52) U.S. Cl.
CPC ...... *A61B 1/00006* (2013.01); *A61B 1/00009* (2013.01); *A61B 1/000094* (2022.02);
(Continued)

(58) Field of Classification Search
CPC ............ A61B 1/00006; A61B 1/00009; A61B 1/000094; G06F 18/2431; G06F 18/0012;
(Continued)

(56) References Cited

U.S. PATENT DOCUMENTS

2006/0274928 A1 12/2006 Collins et al.
2007/0038086 A1* 2/2007 Ohtsuka .............. G01S 7/52073
600/437
(Continued)

FOREIGN PATENT DOCUMENTS

CN 108135457 A 6/2018
EP 2 149 331 A1 2/2010
(Continued)

OTHER PUBLICATIONS

The extended European search report issued by the European Patent Office dated Mar. 22, 2022, which corresponds to European Patent Application No. 19918612.3-1126 and is related to U.S. Appl. No. 17/391,644.

(Continued)

*Primary Examiner* — Casey L Kretzer
(74) *Attorney, Agent, or Firm* — Studebaker & Brackett PC

(57) ABSTRACT

A medical image processing apparatus includes a recognition unit that detects a region of interest from an acquired medical image and classifies the region of interest; a display control unit that causes emphasis display for emphasizing the region of interest and a classification for the region of interest to be displayed in a screen identical to a screen for displaying an observation target included in the medical image; and an observation image switching unit that switches whether to display consecutive images or to display a still image by using a display device. In a case where consecutive image display of an observation image is switched to still image display by the observation image switching unit, the display control unit makes a change for reducing visual recognizability of at least any of the emphasis display or the classification compared with a case of the consecutive image display of the observation image.

20 Claims, 12 Drawing Sheets

(51) Int. Cl.
    *G06T 7/00*         (2017.01)
    *G06V 10/25*      (2022.01)
    *G06V 10/82*      (2022.01)

(52) U.S. Cl.
    CPC ........ *G06F 18/2431* (2023.01); *G06T 7/0012* (2013.01); *G06V 10/25* (2022.01); *G06V 10/82* (2022.01); *G06T 2207/10068* (2013.01); *G06T 2207/20081* (2013.01); *G06T 2207/20084* (2013.01)

(58) Field of Classification Search
    CPC .................. G06V 10/25; G06V 10/82; G06T 2207/10068; G06T 2207/20081; G06T 2207/20084
    See application file for complete search history.

(56) References Cited

U.S. PATENT DOCUMENTS

| | | |
|---|---|---|
| 2015/0078615 A1 | 3/2015 | Staples, II et al. |
| 2015/0187119 A1* | 7/2015 | Masumoto ............ A61B 6/503 345/424 |
| 2016/0331224 A1 | 11/2016 | Uji et al. |
| 2018/0242817 A1 | 8/2018 | Imaizumi et al. |
| 2018/0249900 A1 | 9/2018 | Imaizumi et al. |
| 2019/0282135 A1 | 9/2019 | Ito et al. |
| 2020/0069160 A1 | 3/2020 | Oosake |
| 2020/0126223 A1 | 4/2020 | Kitamura et al. |

FOREIGN PATENT DOCUMENTS

| | | |
|---|---|---|
| EP | 3 357 406 A1 | 8/2018 |
| JP | 2005-124756 A | 5/2005 |
| JP | 2007-209770 A | 8/2007 |
| JP | 2009-105880 A | 5/2009 |
| JP | 2014-054398 A | 3/2014 |
| JP | 2015-097687 A | 5/2015 |
| JP | 2015-167629 A | 9/2015 |
| JP | 2016-174976 A | 10/2016 |
| JP | 2016-214312 A | 12/2016 |
| JP | 2017-060682 A | 3/2017 |
| WO | 2017/073337 A1 | 5/2017 |
| WO | 2017/081976 A1 | 5/2017 |
| WO | 2018/105020 A1 | 6/2018 |
| WO | 2018/198327 A1 | 11/2018 |
| WO | 2018/221033 A1 | 12/2018 |
| WO | 2019/003597 A1 | 1/2019 |

OTHER PUBLICATIONS

International Search Report issued in PCT/JP2019/040362; dated Dec. 17, 2019.
International Preliminary Report on Patentability and Written Opinion issued in PCT/JP2019/040362; dated Aug. 25, 2021.
Krizhevsk et al.: ImageNet Classification with Deep Convolutional Neural Networks, Advances in Neural Information Processing Systems 25, pp. 1-9, (2012).
Sermanet et al.: OverFeat: Integrated Recognition, Localization and Detectionusing Convolutional Networks, ICLR (International Conference on Learning Representations), pp. 1-16, Feb. 24, 2014.
An Office Action mailed by China National Intellectual Property Administration dated Sep. 23, 2023, which corresponds to Chinese Patent Application No. 201980093038.9 and is related to U.S. Appl. No. 17/391,644; with English language translation.

* cited by examiner

MEDICAL IMAGE PROCESSING APPARATUS, PROCESSOR DEVICE, ENDOSCOPE SYSTEM, MEDICAL IMAGE PROCESSING METHOD, AND PROGRAM

CROSS-REFERENCE TO RELATED APPLICATIONS

This application is a Continuation of PCT International Application No. PCT/JP2019/040362 filed on Oct. 15, 2019, which claims priority under 35 U.S.C § 119(a) to Japanese Patent Application No. 2019-042741 filed on Mar. 8, 2019. Each of the above application(s) is hereby expressly incorporated by reference, in its entirety, into the present application.

BACKGROUND OF THE INVENTION

1. Field of the Invention

The present invention relates to a medical image processing apparatus, a processor device, an endoscope system, a medical image processing method, and a program, and more particularly to screen display.

2. Description of the Related Art

A common endoscope system radiates illumination light from a tip of an insertion section of an endoscope, images an observation target by using an imaging element, and obtains image information of the observation target. An image obtained by imaging is displayed on a monitor. A user such as a doctor observes the image displayed on the monitor to perform examination.

In recent years, advanced automatic recognition using deep learning has become available. A. Krizhevsky, I. Sutskever, and G. Hinton, "ImageNet classification with deep convolutional neural networks.", NIPS (Neural Information Processing Systems conference), 2012 describes a technique relating to image recognition using deep learning. It is conceived that an endoscope system also automatically performs detection and classification of a lesion or the like by using a recognizer produced using deep learning. Among these, there is a technique called SSD (Single Shot multi box Detector) described in Pierre Sermanet, David Eigen, Xiang Zhang, Michael Mathieu, Rob Fergus, and Yann LeCun, "OverFeat: Integrated Recognition, Localization and Detection using Convolutional Networks", ICLR (International Conference on Learning Representations), 2014. This technique is known to enable detection and classification or the like to be collectively performed. Note that there may be cases where classification of a lesion or the like is referred to as differentiation.

WO2017/073337A describes an endoscope system that calculates a feature quantity of an observation image, and detects a lesion candidate region on the basis of the feature quantity. The system displays a notification image in a region different from the lesion candidate region in the observation image so as to notify a technician that the lesion candidate region has been detected. The system performs processing of adding a marker image that surrounds the lesion candidate region to the observation image so as to indicate the position of the lesion candidate region.

In the case where an operation switch is changed from an OFF state to an ON state, the system displays a still image, ends the notification process so as to hide the notification image, and starts emphasis display so as to display the marker image. In this manner, a decrease in the technician's attention to the observation image is suppressed.

SUMMARY OF THE INVENTION

However, in the case where a technician pauses and observes a sequentially displayed observation image when automatic detection and automatic classification of a lesion are performed in an endoscopic image, emphasis display indicating detection of the lesion may hinder the observation performed by the technician.

When displaying a still image, the system described in WO2017/073337A starts emphasis display, so that a marker image is displayed. Thus, when the still image is observed, the marker image may hinder the observation.

The present invention is made in view of such circumstances, and an object thereof is to provide a medical image processing apparatus, a processor device, an endoscope system, a medical image processing method, and a program that may avoid a situation in which emphasis display or the like indicating detection of a lesion hinders observation performed by a technician or the like.

In order to achieve the above object, the following aspects of the invention are provided.

A medical image processing apparatus according to a first aspect is a medical image processing apparatus including a recognition unit that detects a region of interest from an acquired medical image and classifies the region of interest; a display control unit that causes emphasis display for emphasizing the region of interest and a classification for the region of interest to be displayed in a screen identical to a screen for displaying an observation target included in the medical image; and an observation image switching unit that switches whether to display consecutive images of an observation image or to display a still image of the observation image by using a display device, in which in a case where consecutive image display of the observation image is switched to still image display by using the observation image switching unit, the display control unit makes a change for reducing visual recognizability of at least any of the emphasis display or the classification compared with a case of the consecutive image display of the observation image.

According to the first aspect, in a case where a user observes the still image of the observation target, a situation may be suppressed in which at least any of the emphasis display or the classification hinders the observation.

A style for visually emphasizing a region of interest may be used to emphasize the region of interest.

The change for reducing visual recognizability of at least any of the emphasis display or the classification may include a style of setting at least any of the emphasis display or the classification to non-display.

The medical image processing apparatus according to the first aspect may include a medical image acquisition unit that acquires a medical image.

In a second aspect, in the medical image processing apparatus according to the first aspect, the display control unit may display the classification in a case where making the change for reducing the visual recognizability of at least any of the emphasis display or the classification compared with the case of the consecutive image display of the observation image.

According to the second aspect, the classification is displayed in a case where the display style of at least any of the emphasis display or the classification is changed. This enables the use of the classification.

In the second aspect, a style for setting the emphasis display to non-display but keeping the display style of the classification unchanged may be used.

In a third aspect, in the medical image processing apparatus according to the first aspect or the second aspect, the display control unit may move a position of at least any of the emphasis display or the classification to a position outside a region where the observation image is displayed in the screen where the observation image is displayed.

According to the third aspect, at least any of the emphasis display or the classification is moved to a position outside the region where the observation image is displayed. Consequently, a situation may be avoided in which at least any of the emphasis display or the classification hinders observation of the still image performed by an observer.

In a fourth aspect, the medical image processing apparatus according to any one of the first aspect to the third aspect may further include a period setting unit that sets a period from a timing at which a display style of at least any of the emphasis display or the classification is changed to a timing at which the display style is returned to an original, in which the display control unit may return the display style to the original in response to an elapse of the period set by using the period setting unit since the timing at which the display style of at least any of the emphasis display or the classification is changed.

According to the fourth aspect, the display style can be returned to the original display style in response to an elapse of a predetermined period since the display style of at least any of the emphasis display or the classification is changed.

In a fifth aspect, the medical image processing apparatus according to any one of the first aspect to the fourth aspect may further include a command signal acquisition unit that acquires a command signal transmitted in a case where an operation section is operated, in which in a case where the command signal acquisition unit acquires a command signal indicating that the consecutive image display of the observation image is to be switched to the still image display, the display control unit may make the change for reducing the visual recognizability of at least any of the emphasis display or the classification compared with the case of the consecutive image display of the observation image.

According to the fifth aspect, at least any of a change in the display style of the region of interest or a change in the display style of the classification for the region of interest may be made in a case where an operation for switching consecutive image display of the observation image to still image display is performed by using the operation section.

In a sixed aspect, in the medical image processing apparatus according to any one of the first aspect to the fifth aspect, the recognition unit may include a plurality of downsizing processing units that perform processing for reducing a size of an input image in stages; and a feature map generation unit that generates a feature map from an output image of each of the plurality of downsizing processing units.

In a seventh aspect, in the medical image processing apparatus according to the sixth aspect, the downsizing processing units may include at least any of a pooling processing unit that performs pooling processing on the input image or a convolutional processing unit that performs convolutional processing on the input image.

According to the seventh aspect, a convolutional neural network may be used in detection and classification of a region of interest.

In an eighth aspect, in the medical image processing apparatus according to the sixth aspect or the seventh aspect, the recognition unit may include a region-of-interest recognition unit that performs at least any of identification of the region of interest or classification of the region of interest from a plurality of the feature maps generated by using the feature map generation unit.

According to the eighth aspect, the feature maps representing features of the input image may be used in at least any of detection of the region of interest or classification of the region of interest.

In a ninth aspect, in the medical image processing apparatus according to the eighth aspect, the region-of-interest recognition unit may perform detection of the region of interest and classification of the region of interest on the basis of an overlapping degree of the plurality of feature maps.

According to the ninth aspect, the region-of-interest detection accuracy and the region-of-interest classification accuracy may improve.

In a tenth aspect, in the medical image processing apparatus according to any one of the first aspect to the ninth aspect, the recognition unit may include a parameter storage unit that stores parameters obtained by collectively learning detection of a region of interest and classification of the region of interest for at least one image.

According to the tenth aspect, a region-of-interest detection process and a region-of-interest classification process may have a part in common.

In an eleventh aspect, in the medical image processing apparatus according to any one of the first aspect to the tenth aspect, the display control unit may use, as the emphasis display, a closed curve that surrounds the region of interest, and in a case where changing the display style of the emphasis display, may change at least any of a color, a density, or a type of a line of the closed curve.

According to the eleventh aspect, in the case where the closed curve is used as the emphasis display, the emphasis display can be weakened efficiently.

In a twelfth aspect, in the medical image processing apparatus according to any one of the first aspect to the eleventh aspect, in a case where changing the display style of the emphasis display, the display control unit may move the emphasis display to a position where visual recognizability of the emphasis display is reduced.

According to the twelfth aspect, a situation may be suppressed in which the emphasis display hinders observation.

In a thirteenth aspect, in the medical image processing apparatus according to any one of the first aspect to the twelfth aspect, the display control unit may use text information representing content of the classification as classification information representing the classification for the region of interest, and in a case where changing the display style of the classification for the region of interest, may move the text information to a position where visual recognizability of the text information is reduced.

According to the thirteenth aspect, a situation may be suppressed in which the text information representing the content of the classification for the region of interest hinders observation.

In a fourteenth aspect, in the medical image processing apparatus according to the thirteenth aspect, in a case where changing the display style of the classification for the region of interest, the display control unit may move the text information to a position outside a display region of an image representing the observation target.

According to the fourteenth aspect, the text information is not superimposed on the image representing the observation target. Thus, a situation may be suppressed in which the text information hinders observation.

In a fifteenth aspect, in the medical image processing apparatus according to the fourteenth aspect, in a case where a plurality of the regions of interest are detected, the display control unit may move a plurality of pieces of the text information representing classifications of the plurality of regions of interest to a position outside the display region of the image representing the observation target while maintaining a positional relationship among the plurality of regions of interest.

According to the fifteenth aspect, the positional relationship among the plurality of regions of interest in the image representing the observation target may be grasped by using the positional relationship among the plurality of classifications.

In a sixteenth aspect, in the medical image processing apparatus according to any one of the thirteenth aspect to the fifteenth aspect, in a case where changing the display style of the classification for the region of interest, the display control unit may cause only an initial of a character string representing a meaning of the classification to be displayed as the text information.

According to the sixteenth aspect, the visual recognizability of the classification may be reduced but the content of the classification may be grasped.

A processor device according to a seventeenth aspect is a processor device including an endoscope control unit that controls an endoscope; a recognition unit that detects a region of interest from a medical image acquired by using the endoscope and classifies the region of interest; a display control unit that causes emphasis display for emphasizing the region of interest and a classification for the region of interest to be displayed in a screen identical to a screen for displaying an observation target included in the medical image; and an observation image switching unit that switches whether to display consecutive images of an observation image or to display a still image of the observation image by using a display device, in which in a case where consecutive image display of the observation image is switched to still image display by using the observation image switching unit, the display control unit makes a change for reducing visual recognizability of at least any of the emphasis display or the classification compared with a case of the consecutive image display of the observation image.

According to the seventeenth aspect, substantially the same advantage as that of the first aspect can be obtained.

The seventeenth aspect may be appropriately combined with any of features that are substantially the same as those specified in the second to sixteenth aspects. In such a case, a constituent element responsible for a process or function specified in the medical image processing apparatus can be grasped as a constituent element responsible for the corresponding process or function in the processor device.

An endoscope system according to an eighteenth aspect is an endoscope system including an endoscope; a processor device that controls the endoscope; and a medical image processing apparatus that performs processing on an endoscopic image acquired by using the endoscope, in which the medical image processing apparatus includes a recognition unit that detects a region of interest from an acquired medical image and classifies the region of interest; a display control unit that causes emphasis display for emphasizing the region of interest and a classification for the region of interest to be displayed in a screen identical to a screen for displaying an observation target included in the medical image; and an observation image switching unit that switches whether to display consecutive images of an observation image or to display a still image of the observation image by using a display device, and in which in a case where consecutive image display of the observation image is switched to still image display by using the observation image switching unit, the display control unit makes a change for reducing visual recognizability of at least any of the emphasis display or the classification compared with a case of the consecutive image display of the observation image.

According to the eighteenth aspect, substantially the same advantage as that of the first aspect can be obtained.

The eighteenth aspect may be appropriately combined with any of features that are substantially the same as those specified in the second to sixteenth aspects. In such a case, a constituent element responsible for a process or function specified in the medical image processing apparatus can be grasped as a constituent element responsible for the corresponding process or function in the endoscope system.

A medical image processing method according to a nineteenth aspect is a medical image processing method including a recognition step of detecting a region of interest from an acquired medical image and classifying the region of interest; a display step of causing emphasis display for emphasizing the region of interest and a classification for the region of interest to be displayed in a screen identical to a screen for displaying an observation target included in the medical image; and an observation image switching step of switching whether to display consecutive images of an observation image or to display a still image of the observation image by using a display device, in which in a case where consecutive image display of the observation image is switched to still image display in the observation image switching step, a change for reducing visual recognizability of at least any of the emphasis display or the classification compared with a case of the consecutive image display of the observation image is made in the display step.

According to the nineteenth aspect, substantially the same advantage as that of the first aspect can be obtained.

The nineteenth aspect may be appropriately combined with any of features that are substantially the same as those specified in the second to sixteenth aspects. In such a case, a constituent element responsible for a process or function specified in the medical image processing apparatus can be grasped as a constituent element responsible for the corresponding process or function in the medical image processing method.

A non-transitory computer readable recording medium storing a program according to a twentieth aspect is a program causing a computer to implement a recognition function that detects a region of interest from an acquired medical image and classifies the region of interest; a display function that causes emphasis display for emphasizing the region of interest and a classification for the region of interest to be displayed in a screen identical to a screen for displaying an observation target included in the medical image; and an observation image switching function that switches whether to display consecutive images of an observation image or to display a still image of the observation image by using a display device, in which in a case where consecutive image display of the observation image is switched to still image display by using the observation image switching function, the display function makes a change for reducing visual recognizability of at least any of the emphasis display or the classification compared with a case of the consecutive image display of the observation image.

According to the twentieth aspect, substantially the same advantage as that of the first aspect can be obtained.

The twentieth aspect may be appropriately combined with any of features that are substantially the same as those specified in the second to sixteenth aspects. In such a case, a constituent element responsible for a process or function specified in the medical image processing apparatus can be grasped as a constituent element responsible for the corresponding process or function in the program.

According to the present invention, in a case where a user observes a still image of an observation target, a situation may be suppressed in which at least any of emphasis display or a classification hinders the observation.

DESCRIPTION OF THE PREFERRED EMBODIMENTS

Preferred embodiments of the present invention will be described in detail below with reference to the accompanying drawings. The same constituent elements are denoted by the same reference signs herein, and redundant description will be appropriately omitted.

Overall Configuration of Endoscope System

Figure 1:
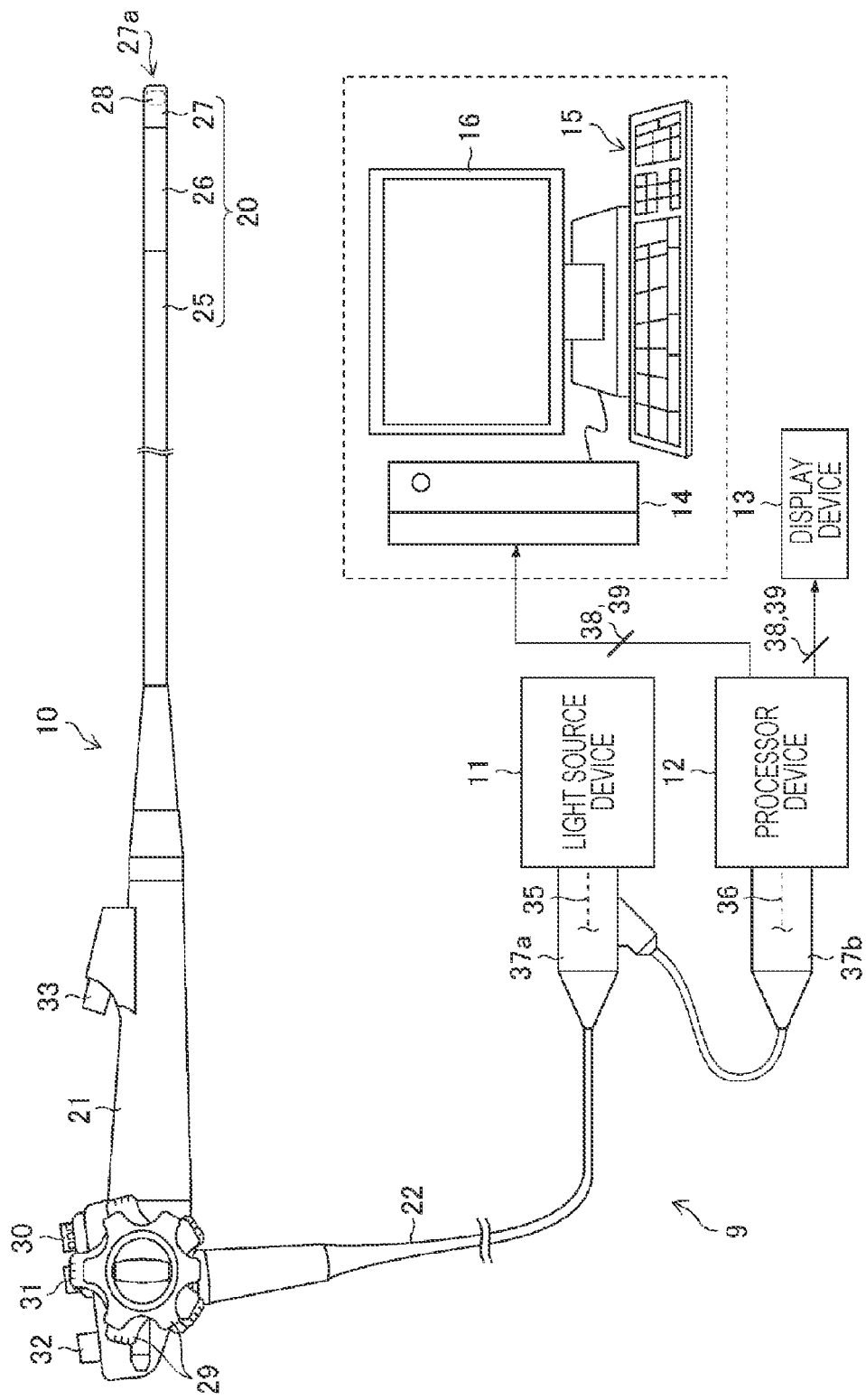
FIG. 1 is an overall configuration diagram of an endoscope system including a medical image processing apparatus according to embodiments.

FIG. 1 is an overall configuration diagram of an endoscope system including a medical image processing apparatus according to embodiments. An endoscope system 9 illustrated in FIG. 1 includes an endoscope 10, a light source device 11, a processor device 12, a display device 13, a medical image processing apparatus 14, an input device 15, and a monitor device 16.

The endoscope 10 illustrated in FIG. 1 is an electronic endoscope and is also a flexible endoscope. The endoscope 10 includes an insertion section 20, an operation section 21, and a universal cord 22. The insertion section 20 is inserted into a subject. The entire insertion section 20 is formed to have an elongated shape with a small diameter.

The insertion section 20 includes a soft part 25, a bending part 26, and a tip part 27. The soft part 25, the bending part 26, and the tip part 27 are coupled to each other to constitute the insertion section 20. The soft part 25 has flexibility sequentially from a proximal end side toward a tip side of the insertion section 20. The bending part 26 has a structure that is bendable in a case where the operation section 21 is operated. The tip part 27 includes an imaging optical system (not illustrated), an imaging element 28, and so on.

A CMOS imaging element or a CCD imaging element is used as the imaging element 28. Note that CMOS is an abbreviation for Complementary Metal Oxide Semiconductor. CCD is an abbreviation for Charge Coupled Device.

An observation window (not illustrated) is provided at a tip surface 27a of the tip part 27. The observation window is an opening formed at the tip surface 27a of the tip part 27. A cover (not illustrated) is attached to the observation window. The imaging optical system (not illustrated) is provided behind the observation window. Image light of a site to be observed is incident onto an imaging surface of the imaging element 28 through the observation window, the imaging optical system, and so on. The imaging element 28 images the image light of the site to be observed incident onto the imaging surface of the imaging element 28 and outputs an imaging signal. The term "imaging" used herein includes the meaning of converting light reflected off from a site to be observed into an electric signal.

The operation section 21 is coupled to the proximal end side of the insertion section 20. The operation section 21 includes various operating members to be operated by a technician. Specifically, the operation section 21 includes two types of bending operation knobs 29. The bending operation knobs 29 are used in a case where an operation of bending the bending part 26 is performed. Note that the technician may include a doctor, an operator, an observer, a user, and the like.

The operation section 21 includes an air/water supply button 30 and a suction button 31. The air/water supply button 30 is used in a case where the technician performs an air/water supply operation. The suction button 31 is used in a case where the technician performs a suction operation.

The operation section 21 includes a still image capturing instruction part 32 and a treatment tool introduction port 33. The still image capturing instruction part 32 includes a button that is operated by the technician in a case where a still image of the site to be observed is captured. The treatment tool introduction port 33 is an opening through which a treatment tool is inserted into a treatment tool insertion path that is inserted inside the insertion section 20. Note that illustration of the treatment tool insertion path and the treatment tool is omitted.

The universal cord 22 is a connection cord that connects the endoscope 10 to the light source device 11. The universal cord 22 includes therein a light guide 35, a signal cable 36, and a fluid tube (not illustrated), which are inserted inside the insertion section 20.

In addition, a tip part of the universal cord 22 includes a connector 37a to be connected to the light source device 11 and a connector 37b branching from the connector 37a and to be connected to the processor device 12.

In a case where the connector 37a is connected to the light source device 11, the light guide 35 and the fluid tube (not illustrated) are inserted into the light source device 11. Consequently, necessary illumination light, a liquid such as water, and a gas such as air are supplied to the endoscope 10 from the light source device 11 through the light guide 35 and the fluid tube (not illustrated).

As a result, the illumination light is radiated from an illumination window (not illustrated) of the tip surface 27a of the tip part 27 toward the site to be observed. In addition, in response to an operation of pressing the air/water supply button 30, a gas or water is ejected from an air/water supply nozzle (not illustrated) of the tip surface 27a of the tip part 27 toward the observation window (not illustrated) of the tip surface 27a. Note that the site to be observed may be referred to as an observation target, an examination target, or the like in some cases.

In a case where the connector 37b is connected to the processor device 12, the signal cable 36 and the processor device 12 are electrically connected to each other. Consequently, an imaging signal of the site to be observed is output from the imaging element 28 of the endoscope 10 to the processor device 12 through the signal cable 36. Also, a control signal is output from the processor device 12 to the endoscope 10 through the signal cable 36.

In the present embodiments, the flexible endoscope is described as an example of the endoscope 10. However, various types of electronic endoscopes capable of capturing a moving image of a site to be observed, such as a rigid endoscope, may be used as the endoscope 10.

The light source device 11 supplies illumination light to the light guide 35 of the endoscope 10 through the connector 37a. White light or light in a specific wavelength range is usable as the illumination light. As the illumination light, white light and light in a specific wavelength range may be used in combination. The light source device 11 is configured to be capable of appropriately selecting, as the illumination light, light in a wavelength range corresponding to an observation purpose.

The white light may be light in a white wavelength range or light in a plurality of wavelength ranges. The specific wavelength range is a range narrower than the white wavelength range. As the light in the specific wavelength range, light in a single wavelength range may be used, or light in a plurality of wavelength ranges may be used. Light in the specific wavelength range may be referred to as special light.

The processor device 12 transmits a command signal to the endoscope 10 through the connector 37b and the signal cable 36 to control operation of the endoscope 10. The processor device 12 also acquires an imaging signal from the imaging element 28 of the endoscope 10 through the connector 37b and the signal cable 36. That is, the processor device 12 uses a predetermined frame rate to acquire an imaging signal output from the endoscope 10.

Figure 3:
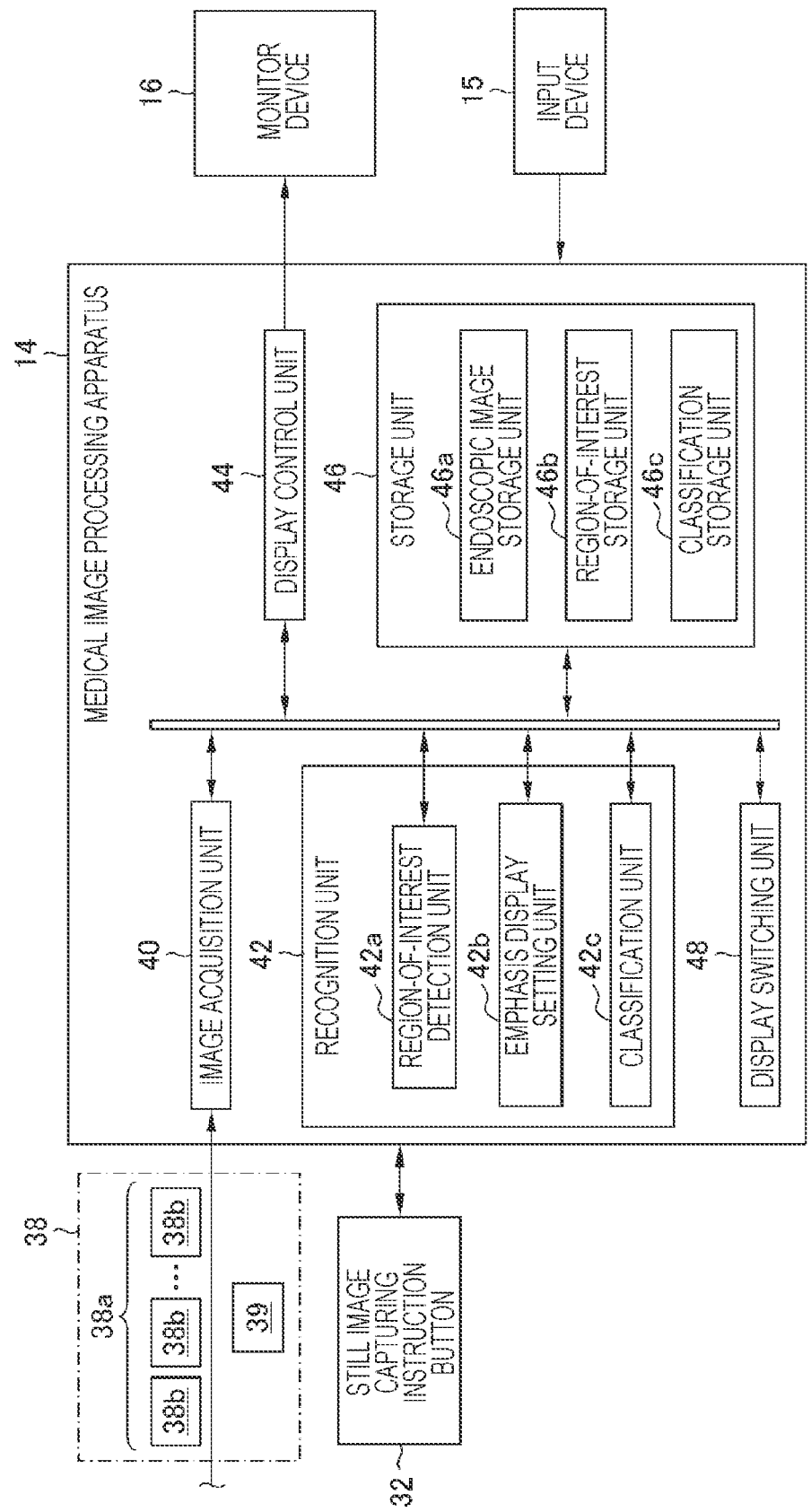
FIG. 3 is a functional block diagram of a medical image processing apparatus according to a first embodiment.

The processor device 12 generates an endoscopic image 38, which is an observation image of the site to be observed, on the basis of the imaging signal acquired from the endoscope 10. Herein, the endoscopic image 38 includes a moving image. The endoscopic image 38 may include a still image 39. Note that a moving image, which is denoted by a reference sign 38a, is illustrated in FIG. 3. The endoscopic image 38 described in the embodiments corresponds to an example of a medical image. In addition, the moving image 38a described in the embodiments corresponds to an example of consecutive images.

In a case where the still image capturing instruction part 32 of the operation section 21 is operated, the processor device 12 generates the still image 39 of the site to be observed on the basis of the imaging signal acquired from the imaging element 28 in parallel with generation of the moving image. The still image 39 may be generated to have a resolution higher than the resolution of the moving image.

In a case where generating the endoscopic image 38, the processor device 12 performs image quality correction in which digital signal processing such as white balance adjustment and shading correction is used. The processor device 12 may add accessory information defined by the DICOM standard to the endoscopic image 38. Note that DICOM is an abbreviation for Digital Imaging and Communications in Medicine. The processor device described in the embodiments corresponds to an example of a processor device including an endoscope control unit that controls an endoscope.

The processor device 12 outputs the endoscopic image 38 to each of the display device 13 and the medical image processing apparatus 14. The processor device 12 may output the endoscopic image 38 to a storage device (not illustrated) via a communication network (not illustrated) in accordance with a communication protocol compliant with the DICOM standard. Note that a communication network 140 illustrated in FIG. 2 may be used as the communication network.

The display device 13 is connected to the processor device 12. The display device 13 displays the endoscopic image 38 transmitted from the processor device 12. The technician may perform an operation of moving the insertion section 20 forward and backward while checking the endoscopic image 38 displayed on the display device 13. Upon detecting a lesion or the like at the site to be observed, the technician may operate the still image capturing instruction part 32 to capture a still image of the site to be observed.

A computer may be used as the medical image processing apparatus 14. A keyboard, a mouse, and the like connectable to the computer are used as the input device 15. The input device 15 and the computer may be connected to each other either with a cable or wirelessly. Various monitors connectable to the computer are used as the monitor device 16.

As the medical image processing apparatus 14, a diagnosis assisting apparatus such as a workstation or a server apparatus may be used. In this case, the input device 15 and the monitor device 16 are provided for each of a plurality of terminals connected to the workstation or the like. Further, as the medical image processing apparatus 14, a medical service assisting apparatus that assists creation of a medical report or the like may be used.

The medical image processing apparatus 14 acquires the endoscopic image 38 and stores the endoscopic image 38. The medical image processing apparatus 14 controls reproduction performed by the monitor device 16. Note that the term "image" used herein includes the meaning of an electric signal representing the image and the meaning of image data such as information representing the image. The term "image" used herein means at least any of an image itself or image data.

Further, the term "storing an image" can be read as "saving an image", "storage of an image", or the like. "Storing an image" used herein means "storing an image in a non-transitory manner". The medical image processing apparatus 14 may include a temporary storage memory that temporarily stores an image.

The input device 15 is used to input an operation instruction for the medical image processing apparatus 14. The monitor device 16 displays the endoscopic image 38 under the control of the medical image processing apparatus 14. The monitor device 16 may function as a display unit of various kinds of information in the medical image processing apparatus 14.

The medical image processing apparatus 14 may be connected to a storage device (not illustrated) via a communication network (not illustrated in FIG. 1). The DICOM standard, a protocol compliant with the DICOM standard, and the like may be used as the image storage format and for the communication between apparatuses via the communication network.

As the storage device (not illustrated), a storage or the like that stores data in a non-transitory manner may be used. The storage device may be managed by using a server apparatus (not illustrated). As the server apparatus, a computer that stores and manages various kinds of data may be used.

Hardware Configuration of Medical Image Processing Apparatus

Figure 2:
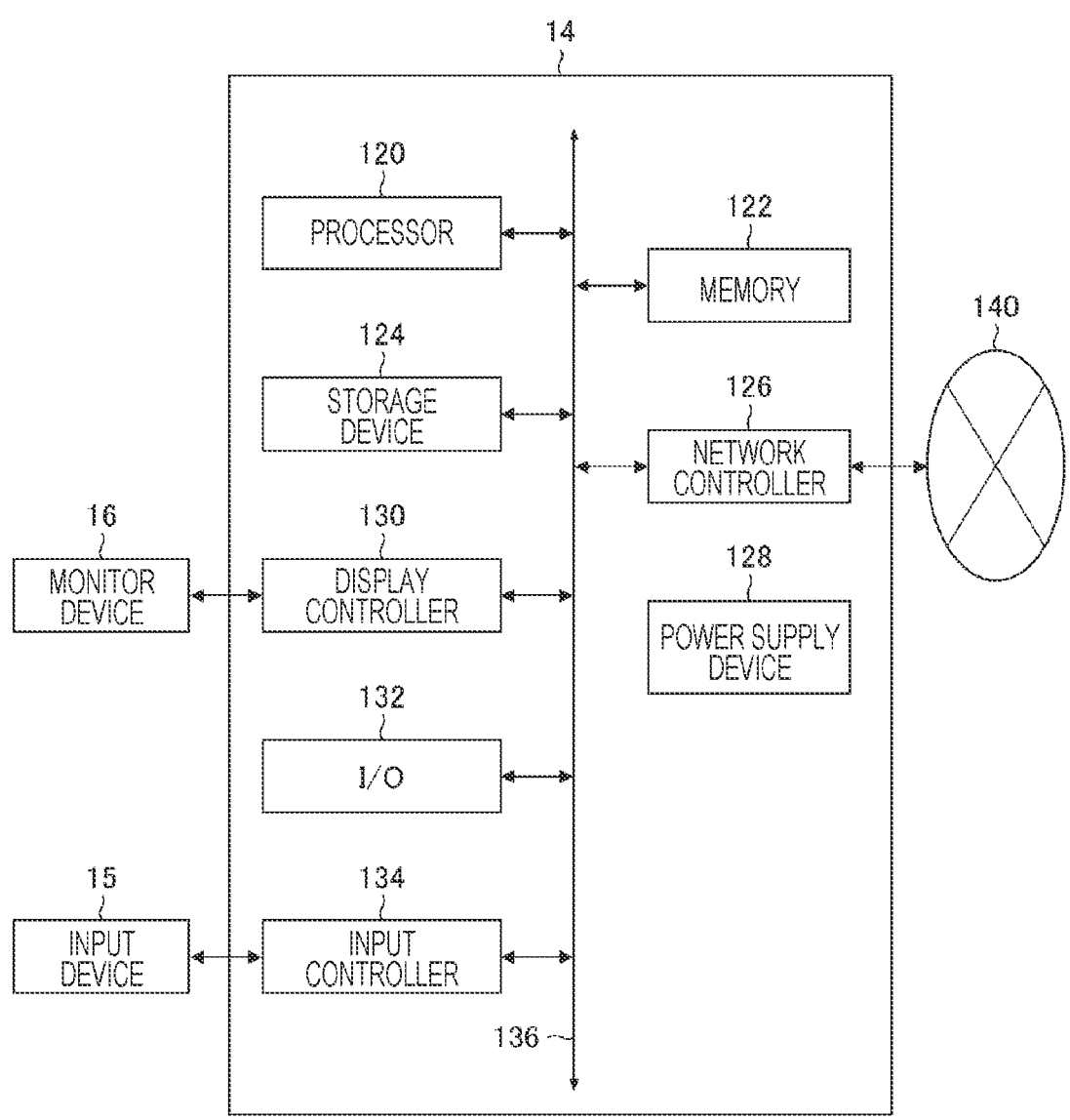
FIG. 2 is a block diagram illustrating a hardware configuration of the medical image processing apparatus.

FIG. 2 is a block diagram illustrating a hardware configuration of the medical image processing apparatus. The medical image processing apparatus 14 illustrated in FIG. 2 includes a processor 120, a memory 122, a storage device 124, a network controller 126, a power supply device 128, a display controller 130, an input/output interface 132, and an input controller 134. Note that I/O illustrated in FIG. 2 represents the input/output interface.

The processor 120, the memory 122, the storage device 124, the network controller 126, the display controller 130, and the input/output interface 132 are connected to each other via a bus 136 so that data communication can be performed therebetween.

Processor

The processor 120 functions as an overall control unit, various calculation units, and a storage control unit of the medical image processing apparatus 14. The processor 120 executes a program stored in a ROM (read only memory) included in the memory 122.

The processor 120 may download a program from an external storage device (not illustrated) via the network controller 126 and execute the downloaded program. The external storage device may be communicably connected to the medical image processing apparatus 14 via the communication network 140.

The processor 120 uses, as a calculation area, a RAM (random access memory) included in the memory 122 and executes various processes in cooperation with various programs. Consequently, various functions of the medical image processing apparatus 14 are implemented.

The processor 120 controls reading out of data from the storage device 124 and writing of data to the storage device 124. The processor 120 may acquire various kinds of data from an external storage device via the network controller 126. The processor 120 is capable of executing various processes such as calculations by using the acquired various kinds of data.

The processor 120 may include one or two or more devices. Examples of the devices include an FPGA (Field Programmable Gate Array), a PLD (Programmable Logic Device), and so on. An FPGA and a PLD are devices whose circuit configurations are changeable after being manufactured.

Other examples of the devices include an ASIC (Application Specific Integrated Circuit). An ASIC includes a circuit configuration dedicatedly designed to perform specific processing.

The processor 120 may use two or more devices of the same kind. For example, the processor 120 may use two or more FPGAs or two or more PLDs. The processor 120 may use two or more devices of different kinds. For example, the processor 120 may use one or more FPGAs and one or more ASICs.

In a case where the medical image processing apparatus 14 includes the plurality of processors 120, the plurality of processors 120 may be configured by using a single device. As an example of configuring the plurality of processors 120 by using a single device, there is a form in which the single device is configured by using a combination of one or more CPUs (Central Processing Units) and software and this device functions as the plurality of processors 120. Note that software used herein is synonymous with a program.

Other examples of configuring the plurality of processors 120 by using a single device include a form in which a device that implements, with a single IC chip, the functions of the entire system including the plurality of processors 120. Representative examples of the device that implements, with a single IC chip, the functions of the entire system including the plurality of processors 120 include a SoC (System On Chip). Note that IC is an abbreviation for Integrated Circuit. As described above, the processor 120 is configured by using one or more of various devices as the hardware structure.

Memory

The memory 122 includes a ROM (not illustrated) and a RAM (not illustrated). The ROM stores various programs to be executed in the medical image processing apparatus 14. The ROM stores parameters, files, and the like used for executing various programs. The RAM functions as a temporary data storage area, a work area for the processor 120, and the like.

Storage Device

The storage device 124 stores various kinds of data in a non-transitory manner. The storage device 124 may be externally attached to the medical image processing apparatus 14. Instead of or along with the storage device 124, a large-capacity semiconductor memory device may be used. The storage device 124 is, for example, a storage device such as an HDD (Hard Disk Drive) or an SSD (Solid State Drive). The storage device 124 may store, for example, an OS (Operating System), an application program, and various kinds of data.

Network Controller

The network controller 126 controls data communication between the medical image processing apparatus 14 and an external apparatus. The control of the data communication may include management of the traffic in the data communication. As the communication network 140 to which the medical image processing apparatus 14 is connected via the network controller 126, a known communication network such as a LAN (Local Area Network) may be used.

Power Supply Device

As the power supply device 128, a large-capacity power supply device such as a UPS (Uninterruptible Power Supply) is used. The power supply device 128 supplies power to each unit of the medical image processing apparatus 14 in a case where the commercial power supply is cut off due to a power failure or the like.

Display Controller

The display controller 130 functions as a display driver that controls the monitor device 16 on the basis of a command signal transmitted from the processor 120.

Input/Output Interface

The input/output interface 132 communicably connects the medical image processing apparatus 14 and an external device to each other. A communication standard such as USB (Universal Serial Bus) may be used for the input/output interface 132.

Input Controller

The input controller 134 converts the format of a signal input by using the input device 15 into a format suitable for processing performed by the medical image processing apparatus 14. Information input from the input device 15 via the input controller 134 is transmitted to each unit via the processor 120.

Note that the hardware configuration of the medical image processing apparatus 14 illustrated in FIG. 2 is merely an example. Thus, addition, deletion, and modification may be appropriately made. In addition, the hardware configuration illustrated in FIG. 2 may also be used for the processor device 12 illustrated in FIG. 1.

Functional Blocks of Medical Image Processing Apparatus

FIG. 3 is a functional block diagram of the medical image processing apparatus according to an embodiment. The medical image processing apparatus 14 includes an image acquisition unit 40, a recognition unit 42, a display control unit 44, a storage unit 46, and a display switching unit 48.

Image Acquisition Unit

The image acquisition unit 40 acquires, from the processor device 12, the endoscopic image 38 obtained by imaging using the endoscope 10. The image acquisition unit 40 stores the endoscopic image 38 in an endoscopic image storage unit 46a.

The image acquisition unit 40 may acquire the endoscopic image 38 from the processor device 12 via an information storage medium such as a memory card. The image acquisition unit 40 may acquire the endoscopic image 38 via the communication network 140 illustrated in FIG. 2.

The image acquisition unit 40 may acquire the moving image 38a constituted by time-series frame images 38b. The image acquisition unit 40 may acquire the still image 39 in the case where still image capturing is performed during capturing of the moving image 38a.

Recognition Unit

The recognition unit 42 includes a region-of-interest detection unit 42a, an emphasis display setting unit 42b, and a classification unit 42c. The recognition unit 42 uses a learning model of a CNN (Convolutional Neural Network) or the like to detect a region of interest from the endoscopic image 38. The recognition unit 42 sets emphasis display for emphasizing the region of interest. The recognition unit 42 uses learning model to classify the region of interest.

The region-of-interest detection unit 42a detects a region of interest from the endoscopic image 38 acquired by using the image acquisition unit 40. The region-of-interest detection unit 42a uses a trained learning model that has performed learning using a pair of the endoscopic image 38 and a region of interest in the endoscopic image 38 as correct answer data. The region-of-interest detection unit 42a stores the region of interest detected from the endoscopic image 38 in a region-of-interest storage unit 46b.

The emphasis display setting unit 42b sets emphasis display for emphasizing the region of interest detected from the endoscopic image 38. The emphasis display setting unit 42b identifies the position and size of the region of interest, and identifies the position and size of emphasis display in accordance with the position and size of the region of interest. The emphasis display setting unit 42b stores emphasis display information including the position and size of the emphasis display in association with the region of interest.

The emphasis display setting unit 42b may use a closed curve surrounding the region of interest as the emphasis display. As the closed curve surrounding the region of interest, a polygon such as a quadrangle surrounding the region of interest, a circle, and a closed curve of any shape may be used. As the closed curve surrounding the region of interest, a polygon or circle circumscribing the region of interest, a polygon or circle that coincides with the region of interest, and a polygon or circuit including the region of interest therein in noncontact manner may be used.

The classification unit 42c classifies the region of interest. For example, the classification unit 42c classifies whether the region of interest is a lesion or a non-lesion. The classification unit 42c may identify a disease name for the region of interest which is a lesion. The classification unit 42c may use standardized classification such as UICC (Union for International Cancer Control) and TNM classification. The classification unit 42c stores a classification for each region of interest in a classification storage unit 46c in association with information on the region of interest.

Note that T of TNM is the initial for tumor. N of TNM is the initial for nodes. M of TNM is the initial for metastasis.

Note that the recognition unit 42 described in the embodiments corresponds to an example of a command signal acquisition unit that acquires a command signal transmitted in a case where an operation section is operated.

Display Control Unit

The display control unit 44 transmits, to the monitor device 16, a display signal representing an image or the like and causing the monitor device 16 to display the endoscopic image 38. The display control unit 44 transmits a display signal representing the region of interest and the classification for the region of interest to the monitor device 16. The display control unit 44 transmits a control signal for the monitor device 16, to the monitor device 16.

The monitor device 16 displays the endoscopic image 38, the region of interest, and the classification for the region of interest. The monitor device 16 may display the region of interest and the classification for the region of interest to be superimposed on the endoscopic image 38. The monitor device 16 may display the region of interest and the classification for the region of interest in a region defined as a region in which the endoscopic image 38 is displayed. The display control unit 44 updates display of the endoscopic image 38, display of the region of interest, and display of the classification for the region of interest by using predetermined update intervals.

Storage Unit

The storage unit 46 includes the endoscopic image storage unit 46a, the region-of-interest storage unit 46b, and the classification storage unit 46c. The endoscopic image storage unit 46a stores the endoscopic image 38 acquired by using the image acquisition unit 40.

The region-of-interest storage unit 46b stores information on the region of interest. The region-of-interest storage unit 46b may store information on the region of interest associated with the endoscopic image 38 from which the region of interest is detected. As the information on the region of interest, coordinate values of the region of interest in the endoscopic image 38 and the shape of the region of interest may be used.

As the coordinate values of the region of interest, the coordinate values of emphasis display used in a case where the emphasis display is set may be used. The shape of the region of interest may include the style of the region of interest and the area of the region of interest.

The classification storage unit 46c stores a classification for each region of interest in association with information on the region of interest. As the information on the region of interest, a number, a symbol, or the like with which the region of interest can be identified may be used.

As the storage unit 46, one or more storage elements may be used. That is, the storage unit 46 may include three storage elements respectively corresponding to the endoscopic image storage unit 46a, the region-of-interest storage unit 46b, and the classification storage unit 46c. As each of the endoscopic image storage unit 46a, the region-of-interest storage unit 46b, and the classification storage unit 46c, a plurality of storage elements may be used. Further, two or all of the endoscopic image storage unit 46a, the region-of-interest storage unit 46b, and the classification storage unit 46c may be constituted by using a single storage element. Note that the storage device 124 illustrated in FIG. 2 can be used as the storage unit 46.

Display Switching Unit

In the case where the medical image processing apparatus 14 acquires a command signal indicating that the technician has operated the still image capturing instruction part 32, the display switching unit 48 changes a display style of the endoscopic image 38 displayed by using the monitor device 16.

Specifically, in the case where the technician has operated the still image capturing instruction part 32, the image acquisition unit 40 acquires captured image data representing the still image 39 of the site to be observed and the display switching unit 48 switches a display screen from moving image display of the site to be observed to still image display.

In a case where switching the observation image from the moving image display to the still image display, the display switching unit 48 changes the display style to a display style for relatively weakening at least any of the emphasis display of the region of interest or the classification for the region of interest.

In the case where a predetermined return condition is satisfied, the display switching unit 48 switches, to an original display style, the changed display style of at least any of the emphasis display of the region of interest or the classification for the region of interest. Examples of the predetermined return condition include a case where the still image display is switched to the moving image display.

Examples of changing the display style of the emphasis display include reducing the density of the emphasis display to make the emphasis display fainter, changing the color of the emphasis display to a lighter color, changing the solid line to a broken line or the like in a case where the solid-line closed curve is used, moving the emphasis display, and setting the emphasis display to non-display.

Examples of changing the display style of the classification for the region of interest include reducing the density of characters representing the classification, changing the color of characters representing the classification to a lighter color, reducing the size of the characters representing the classification, moving characters representing the classification, and setting the characters representing the classification to non-display. Other examples of changing the display style of the classification for the region of interest include omitting part of the character string representing the classification, changing the character string to a picture or icon, etc. Examples of omitting part of the character string include using an abbreviation for the character string, using the initial for the character string, etc.

Note that the display switching unit 48 described in the embodiments corresponds to an example of an observation image switching unit that switches whether to display a moving image of an observation image or to display a still image of the observation image by using a display device.

Procedure of Medical Image Processing Method

Figure 4:
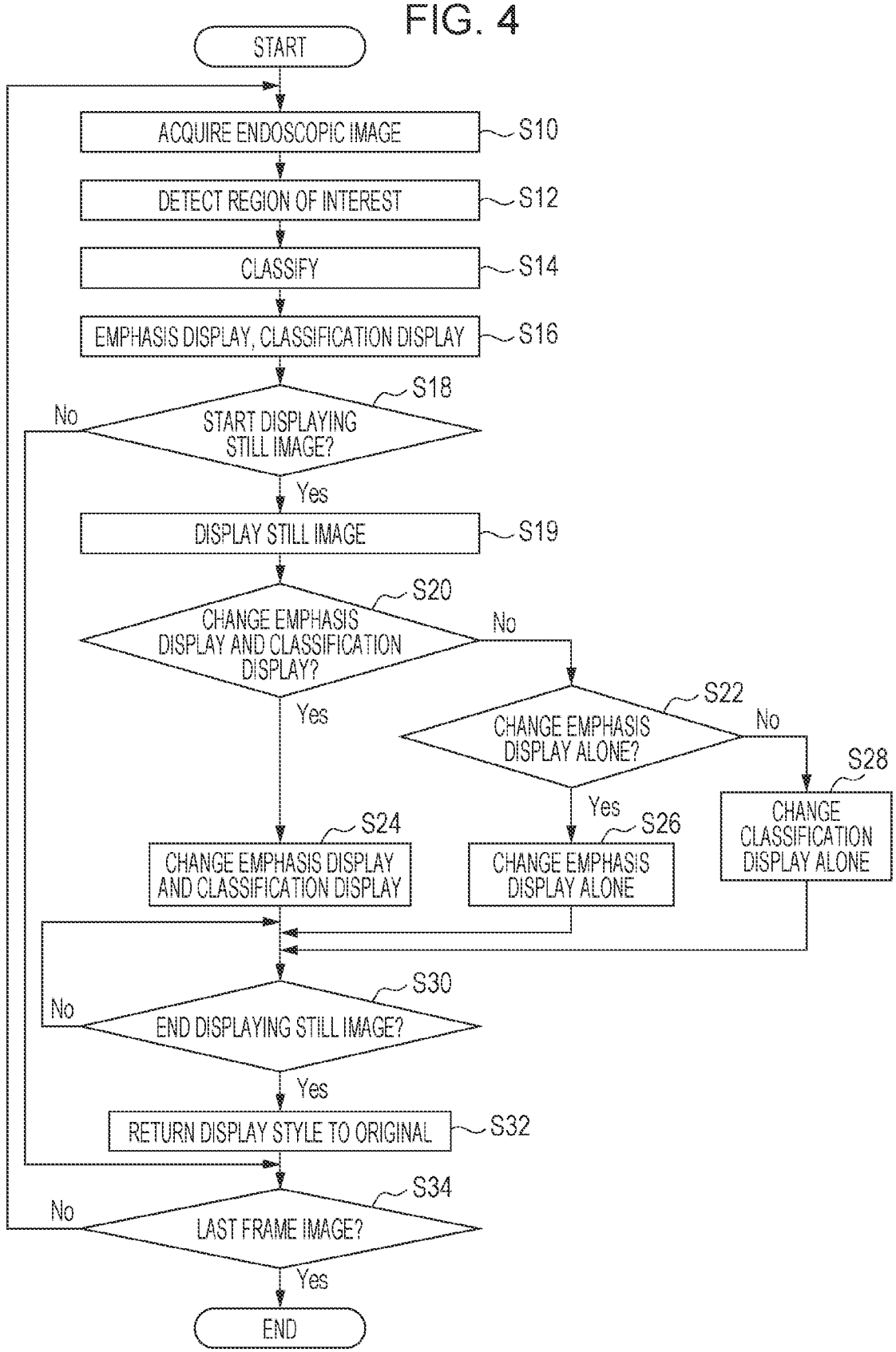
FIG. 4 is a flowchart illustrating a procedure of a medical image processing method according to the first embodiment.

FIG. 4 is a flowchart of a procedure of a medical image processing method according to the embodiment. The medical image processing method described below may be used for the endoscopic image 38 acquired in an examination performed using the endoscope 10 or may be used for the endoscopic image 38 acquired from a medical image server or the like.

In an endoscopic image acquisition step S10, the image acquisition unit 40 illustrated in FIG. 3 acquires the endoscopic image 38 from the processor device 12 illustrated in FIG. 1. In the endoscopic image acquisition step S10, the image acquisition unit 40 stores the endoscopic image 38 in the endoscopic image storage unit 46a. After the endoscopic image acquisition step S10, the process proceeds to a region-of-interest detection step S12.

In the region-of-interest detection step S12, the region-of-interest detection unit 42a detects a region of interest from any of the frame images 38b of the moving image 38a that constitutes the endoscopic image 38. The region-of-interest detection unit 42a may detect a plurality of regions of interest from a single frame image 38b.

In the region-of-interest detection step S12, the region-of-interest detection unit 42a may detect a region of interest from all the frame images 38b of the moving image 38a or may detect a region of interest from the frame images 38b at predetermined intervals.

In the region-of-interest detection step S12, the region-of-interest detection unit 42a stores the region of interest in the region-of-interest storage unit 46b in association with information on the frame image 38b. After the region-of-interest detection step S12, the process proceeds to a classification step S14. Note that the region-of-interest detection step S12 corresponds to an example of a recognition step of detecting a region of interest.

In the classification step S14, the classification unit 42c classifies each region of interest. In the classification step S14, the classification unit 42c stores a classification for each region of interest in the classification storage unit 46c in association with the region of interest. After the classification step S14, the process proceeds to a display step S16. Note that the classification step S14 corresponds to an example of a recognition step of classifying a region of interest.

In the display step S16, the emphasis display setting unit 42b sets emphasis display for each region of interest and transmits information on the emphasis display to the display control unit 44. The display control unit 44 causes emphasis display to be displayed in the screen displaying the endoscopic image 38.

In the display step S16, the classification unit 42c transmits information on the classification for each region of interest to the display control unit 44. The display control unit 44 causes the classification for each region of interest to be displayed in the screen displaying the endoscopic image

38. After the display step S16, the process proceeds to a whether-to-start-still-image-display determining step S18.

In the whether-to-start-still-image-display determining step S18, the display switching unit 48 determines whether the technician has operated the still image capturing instruction part 32. If the display switching unit 48 determines that the still image capturing instruction part 32 is not operated in the whether-to-start-still-image-display determining step S18, No is determined and the moving image display is continued. The process proceeds to a last frame image determining step S34.

On the other hand, if the display switching unit 48 determines that the still image capturing instruction part 32 is operated in the whether-to-start-still-image-display determining step S18, Yes is determined. The process proceeds to a still image display step S19.

In the still image display step S19, the display switching unit 48 switches the observation image from the moving image display to the still image display. After the still image display step S19, the process proceeds to a first change determining step S20. Note that the still image display step S19 described in the embodiments corresponds to an example of an observation image switching step of switching moving image display of an observation image to still image display.

In the first change determining step S20, the display switching unit 48 determines whether to change the display styles of the emphasis display and the classification. If the display switching unit 48 determines to change the display style of either the emphasis display or the classification in the first change determining step S20, No is determined. The process proceeds to a second change determining step S22.

On the other hand, if the display switching unit 48 determines to change the display styles of the emphasis display and the classification in the first change determining step S20, Yes is determined. The process proceeds to a first display style change step S24. In the first display style change step S24, the display switching unit 48 transmits, to the display control unit 44, a command signal indicating that the display styles of the emphasis display and the classification are to be changed.

The display control unit 44 transmits, to the monitor device 16, a display control signal representing a still image and the emphasis display and the classification whose display styles are changed. The monitor device 16 displays the still image 39 and changes the display styles to display styles for relatively weakening the emphasis display and the classification. After the first display style change step S24, the process proceeds to a whether-to-end-still-image-display determining step S30.

In the second change determining step S22, the display switching unit 48 determines whether to change the display style of the emphasis display alone or to change the display style of the classification alone. If the display switching unit 48 determines to change the display style of the emphasis display alone in the second change determining step S22, Yes is determined. The process proceeds to a second display style change step S26.

In the second display style change step S26, the display switching unit 48 transmits, to the display control unit 44, a command signal indicating that the display style of the emphasis display is to be changed. The display control unit 44 transmits, to the monitor device 16, a display control signal representing a still image and the emphasis display whose display style is changed. The monitor device 16 displays the still image 39 and changes the display style to a display style for relatively weakening the emphasis display. After the second display style change step S26, the process proceeds to the whether-to-end-still-image-display determining step S30.

On the other hand, if the display switching unit 48 determines to change the display style of the classification alone in the second change determining step S22, No is determined. The process proceeds to a third display style change step S28. In the third display style change step S28, the display switching unit 48 transmits, to the display control unit 44, a command signal indicating that the display style of the classification is to be changed. The display control unit 44 transmits, to the monitor device 16, a display control signal representing a still image and the classification whose display style is changed. The monitor device 16 displays the still image 39 and changes the display style to a display style for relatively weakening the classification. After the third display style change step S28, the process proceeds to the whether-to-end-still-image-display determining step S30.

In the whether-to-end-still-image-display determining step S30, the display switching unit 48 determines whether a command signal indicating that the still image display is to be ended is acquired. If the display switching unit 48 has not acquired the command signal indicating that the still image display is to be ended in the whether-to-end-still-image-display determining step S30, No is determined. The whether-to-end-still-image-display determining step S30 is performed until Yes is determined in the whether-to-end-still-image-display determining step S30.

On the other hand, if the display switching unit 48 has acquired the command signal indicating that the still image display is to be ended in the whether-to-end-still-image-display determining step S30, Yes is determined. The process proceeds to a display return step S32.

In the display return step S32, the display switching unit 48 transmits, to the display control unit 44, a command signal indicating that at least any of the emphasis display or the classification that has been switched in the first display style change step S24, the second display style change step S26, and the third display style change step S28 is to be returned to the original.

The display control unit 44 transmits, to the monitor device 16, a display signal representing a moving image and a display signal representing the emphasis display and the classification that correspond to the moving image. The monitor device 16 displays the moving image and the emphasis display and the classification that correspond to the moving image. After the display return step S32, the process proceeds to the last frame image determining step S34.

In the last frame image determining step S34, the medical image processing apparatus 14 determines whether the displayed endoscopic image 38 is the last frame image. If the medical image processing apparatus 14 determines that the displayed endoscopic image 38 is not the last frame image in the last frame image determining step S34, No is determined and the process proceeds to the endoscopic image acquisition step S10. Thereafter, the individual steps from the endoscopic image acquisition step S10 to the last frame image determining step S34 are performed until Yes is determined in the last frame image determining step S34.

On the other hand, if the medical image processing apparatus 14 determines that the displayed endoscopic image 38 is the last frame image in the last frame image determining step S34, Yes is determined and the medical image processing apparatus 14 ends the medical image processing method.

Specific Examples of Changing Display Style of Emphasis Display and Changing Display Style of Classification Specific examples of changing the display style of the emphasis display and changing the display style of the classification will be described next. In the following description, any of the frame images 38*b* in the moving image 38*a* obtained by observing the large intestine by using the endoscope 10 illustrated in FIG. 1 is presented as an example. Note that the observation target is not limited to the large intestine, and the gullet, the stomach, the small intestine, and so on may be set as observation targets.

Figure 5:
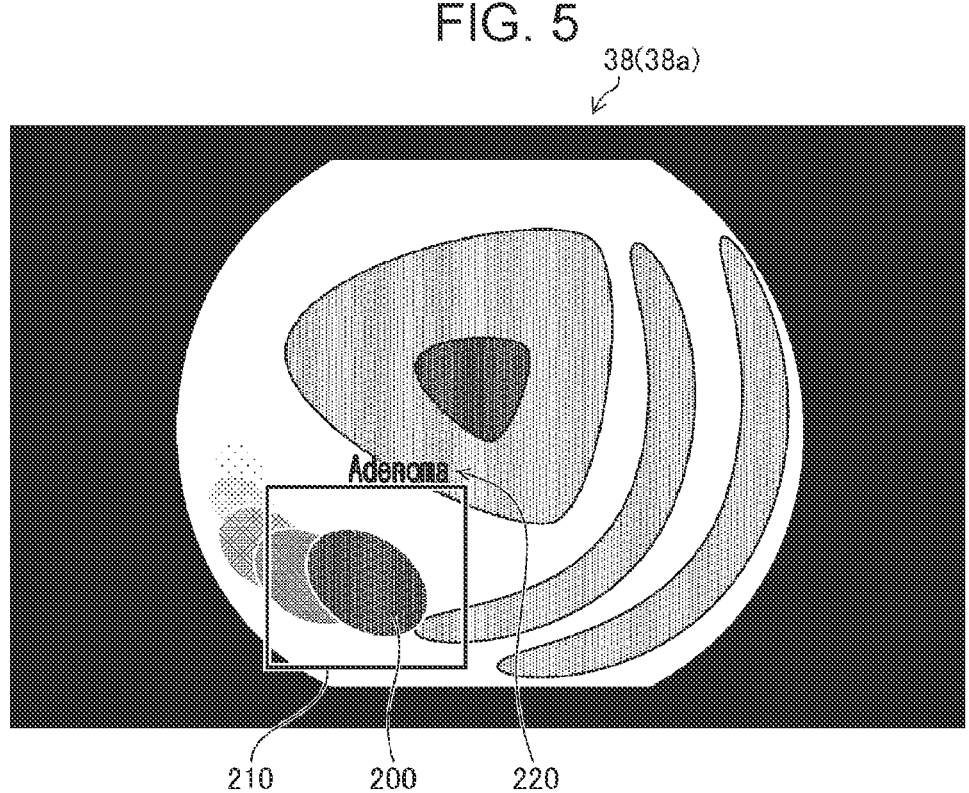
FIG. 5 is an explanatory diagram of emphasis display of a region of interest and classification display of the region of interest.

Specific Examples of Changing Display Styles of Emphasis Display and Classification FIG. 5 is an explanatory diagram of emphasis display of a region of interest and classification display of the region of interest. The endoscopic image 38 illustrated in FIG. 5 is the moving image 38*a*, on which a bounding box 210 that is emphasis display of a lesion 200 and a classification 220 for the lesion 200 are displayed to be superimposed. Text information is used as the classification 220.

Note that the classification 220 illustrated in FIG. 5 corresponds to an example of a classification for which text information representing content of a classification is used as classification information representing the classification for a region of interest.

Figure 6:
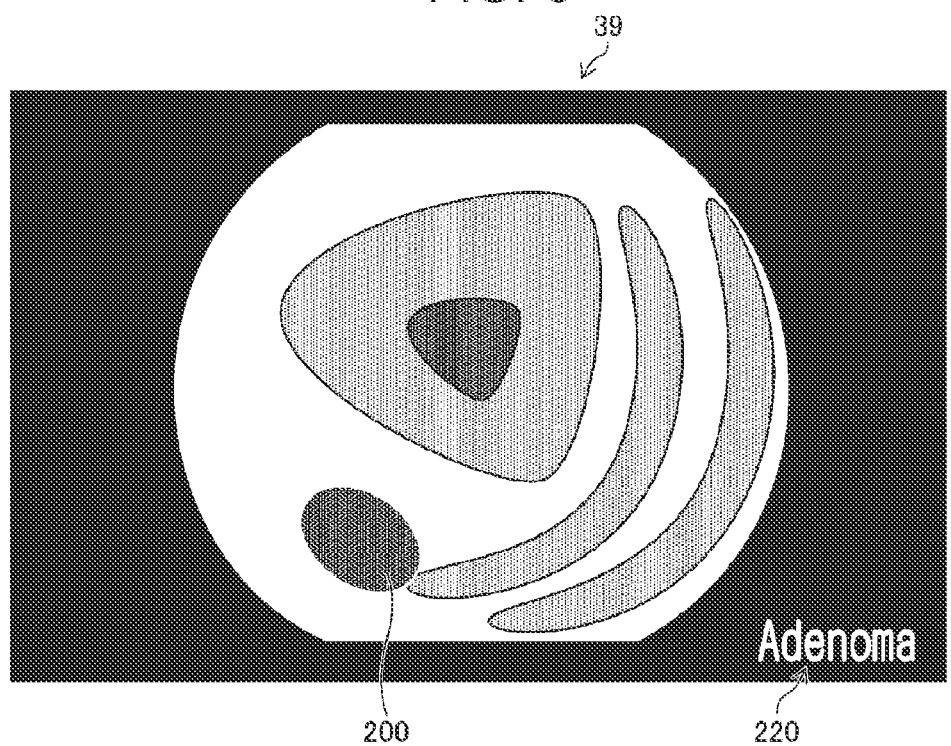
FIG. 6 is an explanatory diagram of the emphasis display of the region of interest and the classification display of the region of interest in a case where a freeze operation is performed.

FIG. 6 is an explanatory diagram of the emphasis display of the region of interest and the classification display of the region of interest in a case where a freeze operation is performed. The still image 39 illustrated in FIG. 6 is a still image corresponding to the moving image 38*a* illustrated in FIG. 5.

In the still image 39 illustrated in FIG. 6, the display style of the bounding box 210 illustrated in FIG. 5 is changed to non-display. In addition, in the still image 39 illustrated in FIG. 6, the display position of the classification 220 is moved to a position outside a region where an image representing the observation target is displayed.

Figure 7:
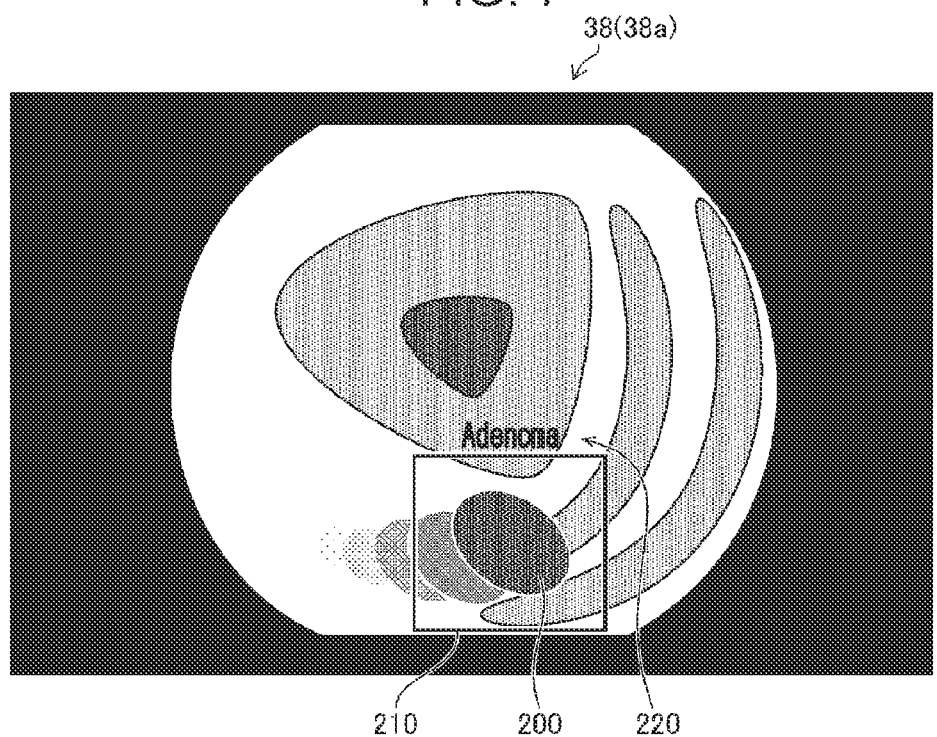
FIG. 7 is an explanatory diagram of the emphasis display of the region of interest and the classification display of the region of interest in a case where the freeze operation is canceled.

FIG. 7 is an explanatory diagram of the emphasis display of the region of interest and the classification display of the region of interest in a case where the freeze operation is canceled. The endoscopic image 38 illustrated in FIG. 7 is the moving image 38*a*, and the bounding box 210 and the classification 220 are displayed to be superimposed on the lesion 200.

Note that the endoscopic image 38 illustrated in FIG. 7 is the frame image 38*b* that is subsequent to the frame image 38*b* of the endoscopic image 38 illustrated in FIG. 5 by one or more frames. Note that illustration of the reference sign 38*b* representing the frame image is omitted in FIGS. 5 and 7.

Effects of Medical Image Processing Apparatus and Medical Image Processing Method According to First Embodiment With the medical image processing apparatus and the medical image processing method according to the first embodiment, the following effects may be obtained.

[1]

In observation of the moving image 38*a* of the endoscopic image 38, the bounding box 210 for emphasizing a region of interest that is the lesion 200 and the classification 220 for the region of interest are displayed. In the case where the still image capturing instruction part 32 is operated, the observation image is switched from the moving image 38*a* to the still image 39. The display style of the still image 39 is changed such that visual recognizability of at least any of the bounding box 210 or the classification 220 is relatively reduced compared with the case where the moving image is displayed. Consequently, a situation may be avoided in which at least any of the bounding box 210 or the classification 220 hinders observation of the still image performed by an observer.

[2]

In changing the display style such that the visual recognizability of the bounding box 210 and the classification 220 is reduced compared with the case where the moving image is displayed, changing the bounding box 210 to non-display and changing a display position of the classification 220 may be used. This enables the use of the classification 220 in observation of the still image.

Figure 8:
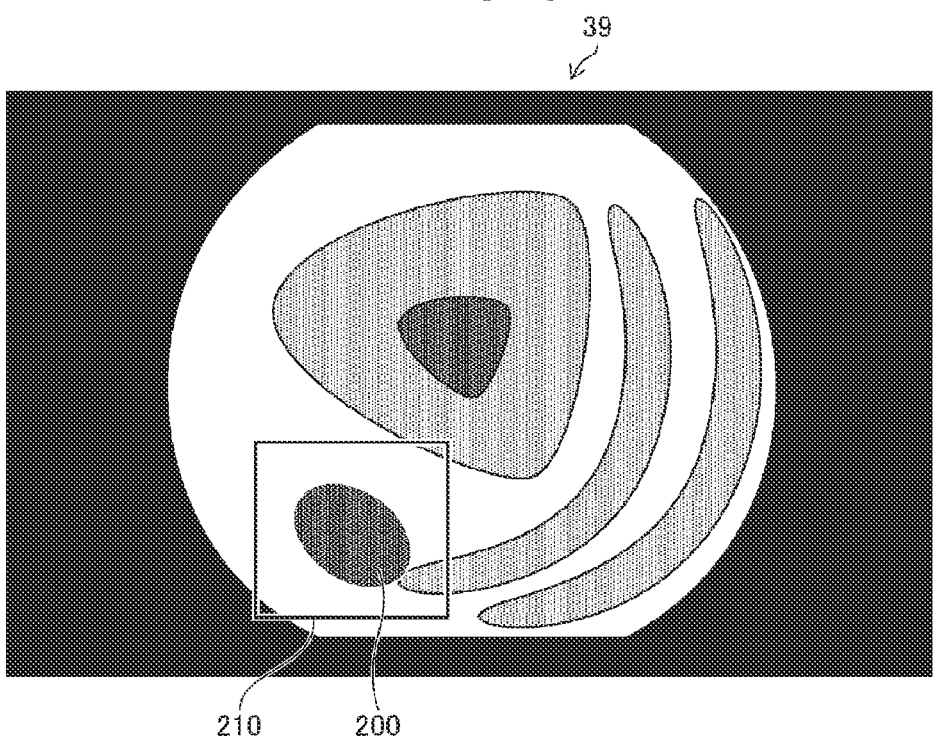
FIG. 8 is an explanatory diagram of emphasis display of a region of interest and classification display of the region of interest in a case where a freeze operation is performed in a first modification.

Modifications of Changing Display Styles of Emphasis Display and Classification First Modification FIG. 8 is an explanatory diagram of emphasis display of a region of interest and classification display of the region of interest in a case where a freeze operation is performed in a first modification. In the still image 39 illustrated in FIG. 8, the display style of the classification 220 illustrated in FIG. 5 is changed to non-display. On the other hand, in the still image 39 illustrated in FIG. 8, the display style of the bounding box 210 is not changed.

According to the first modification, the display of the classification is prevented from hindering observation performed by an observer and the use of the emphasis display is enabled. Note that the display style of the bounding box 210 may be changed together in the first modification.

Second Modification

Figure 9:
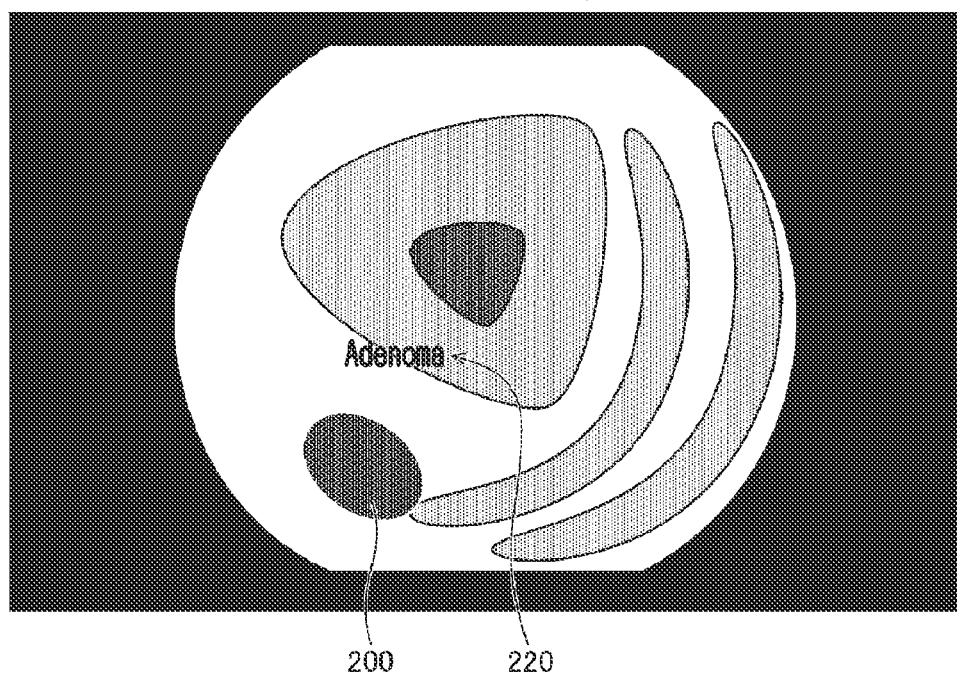
FIG. 9 is an explanatory diagram of emphasis display of a region of interest and a classification display of the region of interest in a case where a freeze operation is performed in a second modification.

FIG. 9 is an explanatory diagram of emphasis display of a region of interest and a classification display of the region of interest in a case where a freeze operation is performed in a second modification. In the still image 39 illustrated in FIG. 9, the display style of the bounding box 210 illustrated in FIG. 5 is changed to non-display. On the other hand, in the still image 39 illustrated in FIG. 9, the display style of the classification 220 is not changed.

According to the second modification, the emphasis display is prevented from hindering observation performed by an observer and the use of the classification is enabled. Note that the display style of the classification 220 may be changed together in the second modification.

Third Modification

Figure 10:
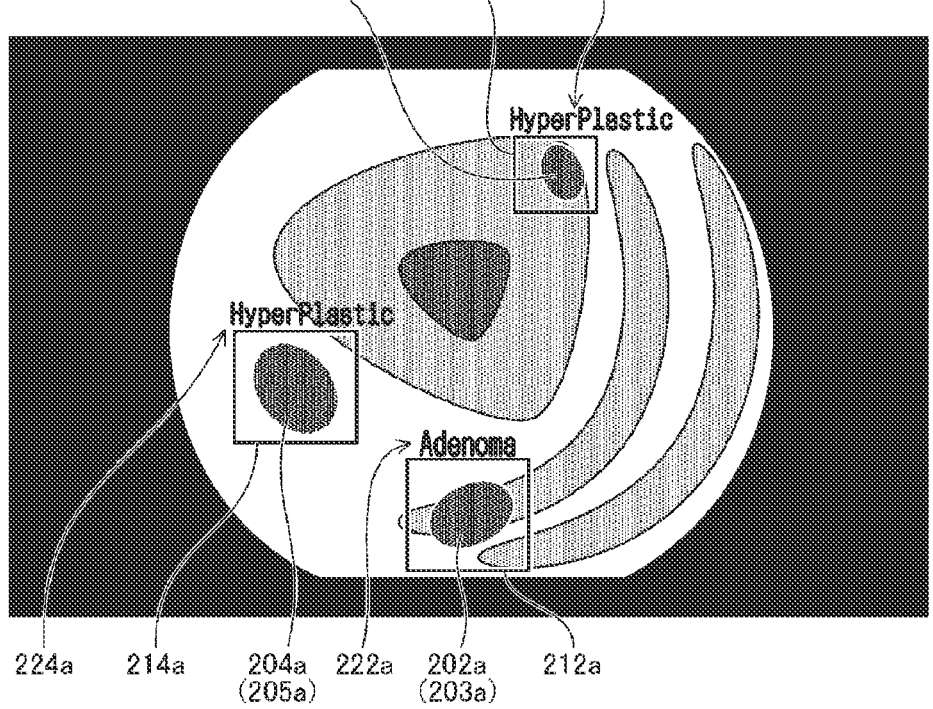
FIG. 10 is an explanatory diagram of a change in a display style of emphasis display in a third modification.

FIG. 10 is an explanatory diagram of a change in a display style of emphasis display in a third modification. In the still image 39 illustrated in FIG. 10, a first bounding box 210*a* and a first classification 220*a* are displayed to be superimposed on a first region of interest 201*a* corresponding to a first lesion 200*a*.

Likewise, a second bounding box 212*a* and a second classification 222*a* are displayed to be superimposed on a second region of interest 203*a* corresponding to a second lesion 202*a*. Further, a third bounding box 214*a* and a third classification 224*a* are displayed to be superimposed on a third region of interest 205*a* corresponding to a third lesion 204*a*.

The first bounding box 210*a*, the second bounding box 212*a*, and the third bounding box 214*a* have a reduced density and are faint compared with the bounding box 210 illustrated in FIG. 5. On the other hand, the density of the first classification 220*a*, the second classification 222*a*, and the third classification 224*a* is not changed compared with that of the classification 220 illustrated in FIG. 5.

According to the third modification, as a style for reducing the degree of emphasis of emphasis display, a style for reducing the density of the emphasis display may be used. Consequently, visual recognizability of the emphasis display may be reduced and a situation may be avoided in which the emphasis display hinders observation performed by an observer. In addition, the use of both the emphasis display and the classification is enabled.

Fourth Modification

Figure 11:
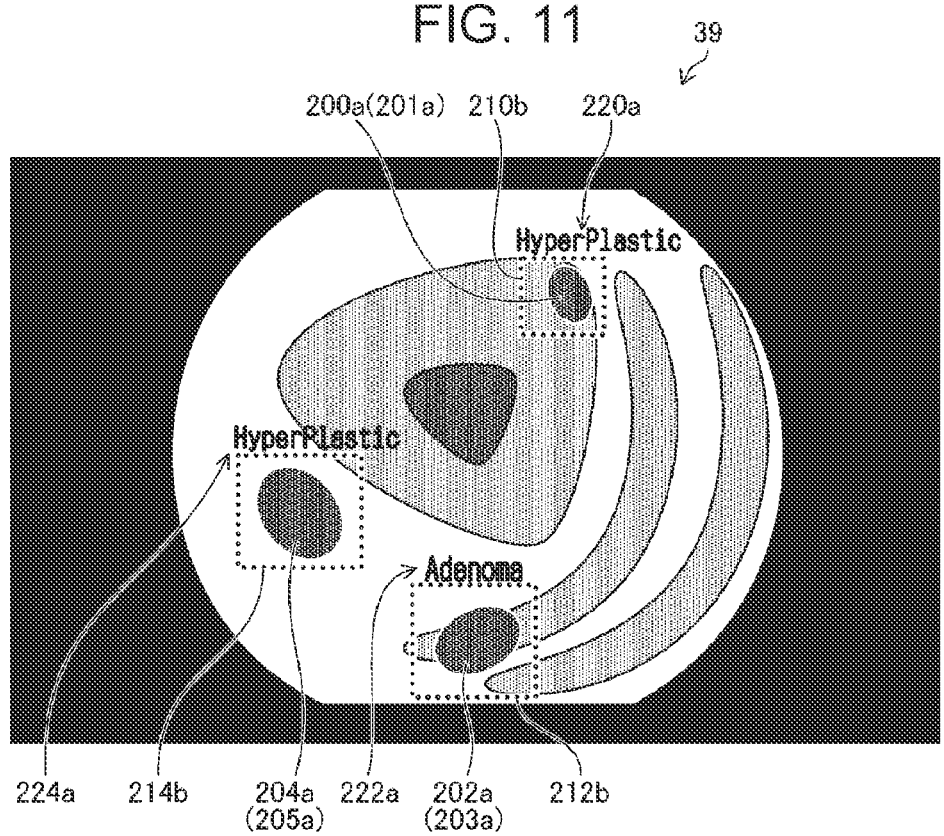
FIG. 11 is an explanatory diagram of a change in a display style of emphasis display in a fourth modification.

FIG. 11 is an explanatory diagram of a change in a display style of emphasis display in a fourth modification. In the still image 39 illustrated in FIG. 11, a fourth bounding box 210b and the first classification 220a are displayed to be superimposed on the first region of interest 201a corresponding to the first lesion 200a.

Likewise, a fifth bounding box 212b and the second classification 222a are displayed to be superimposed on the second region of interest 203a corresponding to the second lesion 202a. Further, a sixth bounding box 214b and the third classification 224a are displayed to be superimposed on the third region of interest 205a corresponding to the third lesion 204a.

The type of a line is changed and a dotted line is used for the fourth bounding box 210b, the fifth bounding box 212b, and the sixth bounding box 214b compared with the bounding box 210 illustrated in FIG. 5. On the other hand, there is no change in the first classification 220a, the second classification 222a, and the third classification 224a from the classification 220 illustrated in FIG. 5.

According to the fourth modification, as the style for reducing the degree of emphasis of emphasis display, a style for changing the type of the line of the emphasis display may be used. Consequently, visual recognizability of the emphasis display may be reduced and a situation may be avoided in which the emphasis display hinders observation performed by an observer. In addition, the use of both the emphasis display and the classification is enabled.

Fifth Modification

Figure 12:
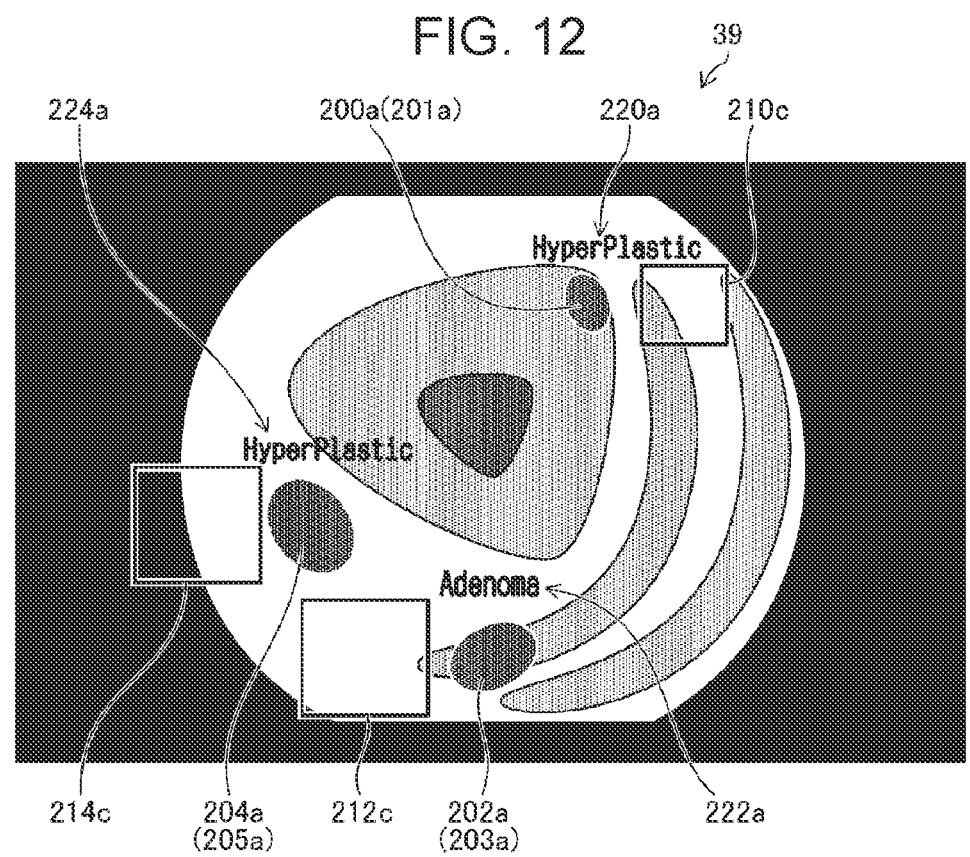
FIG. 12 is an explanatory diagram of a change in a display style of emphasis display in a fifth modification.

FIG. 12 is an explanatory diagram of a change in a display style of emphasis display in a fifth modification. In the still image 39 illustrated in FIG. 12, a seventh bounding box 210c and the first classification 220a are displayed to be superimposed on the first region of interest 201a corresponding to the first lesion 200a.

Likewise, an eighth bounding box 212c and the second classification 222a are displayed to be superimposed on the second region of interest 203a corresponding to the second lesion 202a. Further, a ninth bounding box 214c and the third classification 224a are displayed to be superimposed on the third region of interest 205a corresponding to the third lesion 204a.

The seventh bounding box 210c is disposed at a position where the seventh bounding box 210c does not surround the first region of interest 201a. In addition, the eighth bounding box 212c is disposed at a position where the eighth bounding box 212c does not surround the second region of interest 203a. Further, the ninth bounding box 214c is disposed at a position where the ninth bounding box 214c does not surround the third region of interest 205a.

According to the fifth modification, as the style for reducing the degree of emphasis of emphasis display, a style for changing the position of the emphasis display to the position where the emphasis display does not surround a feature region may be used. Consequently, visual recognizability of the emphasis display may be reduced and a situation may be avoided in which the emphasis display hinders observation performed by an observer. In addition, the use of both the emphasis display and the classification is enabled. Note that the style for changing the position of the emphasis display to the position where the emphasis display does not surround a feature region may include a change to a position where an emphasized region surround part of the feature region.

Sixth Modification

Figure 13:
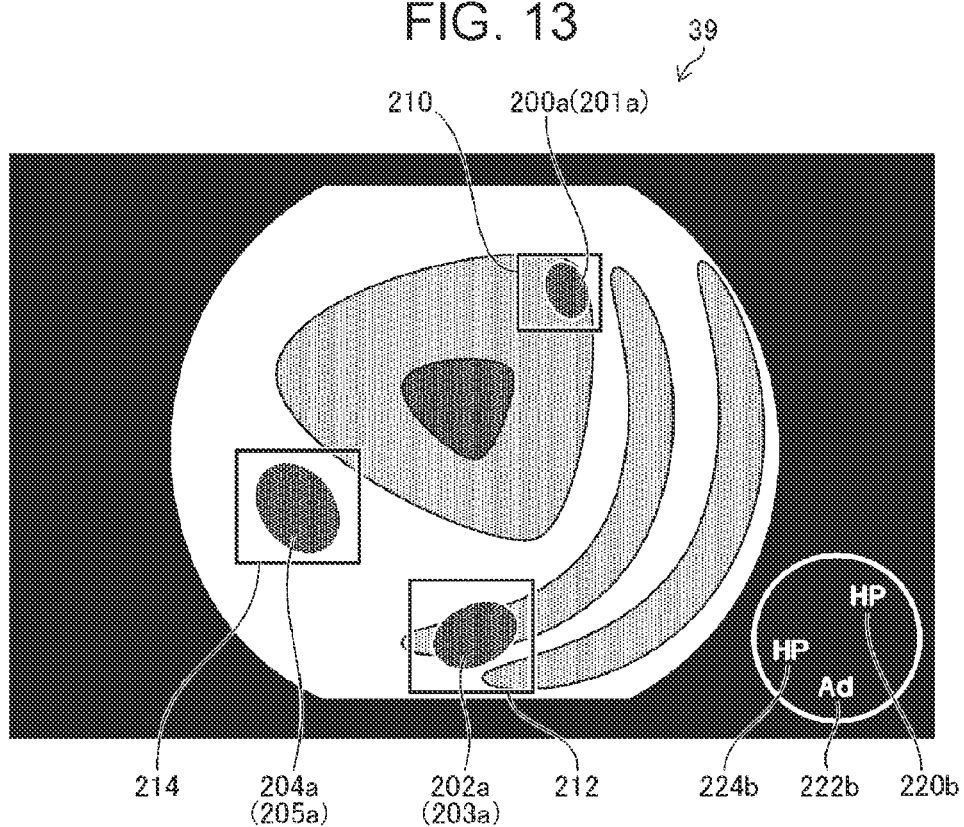
FIG. 13 is an explanatory diagram of a change in a display style of classifications in a sixth modification.

FIG. 13 is an explanatory diagram of a change in a display style of classifications in a sixth modification. In the still image 39 illustrated in FIG. 13, a fourth classification 220b indicating the classification for the first region of interest 201a corresponding to the first lesion 200a, a fifth classification 222b indicating the classification for the second region of interest 203a corresponding to the second lesion 202a, and a sixth classification 224b indicating the classification for the third region of interest 205a corresponding to the third lesion 204a are moved to positions where the fourth classification 220b, the fifth classification 222b, and the sixth classification 224b are not superimposed on the observation image in the still image 39.

In addition, a positional relationship among the first classification 220a, the second classification 222a, and the third classification 224a illustrated in FIG. 10 is maintained as a positional relationship among the fourth classification 220b, the fifth classification 222b, and the sixth classification 224b.

Further, an abbreviation for omitting part of the character string used for the first classification 220a is used as the fourth classification 220b. Likewise, an abbreviation for omitting part of the character string used for the second classification 222a is used as the fifth classification 222b. An abbreviation for omitting part of the character string used for the third classification 224a is used as the sixth classification 224b.

Note that the reference sign 210 illustrated in FIG. 13 denotes a bounding box displayed before the display style change of the first bounding box 210a illustrated in FIG. 10. The reference sign 212 denotes a bounding box displayed before the display style change of the second bounding box 212a. The reference sign 214 denotes a bounding box displayed before the display style change of the third bounding box 214a. The same applies to FIG. 14.

According to the sixth modification, as the style for reducing visual recognizability of a classification, a style of changing text information representing the classification to a position where the text information is not superimposed on the observation image may be used. Consequently, visual recognizability of the classification may be reduced and a situation may be avoided in which the classification hinders observation performed by an observer. In addition, the use of both the emphasis display and the classification is enabled.

Seventh Modification

Figure 14:
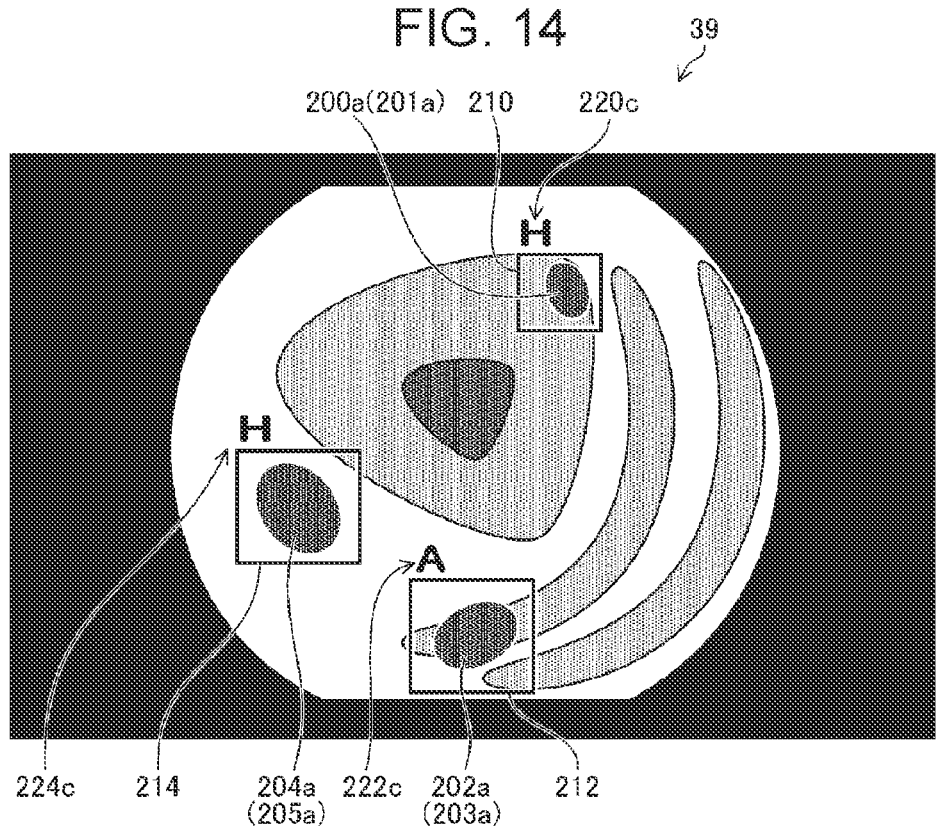
FIG. 14 is an explanatory diagram of a change in a display style of classifications in a seventh modification.

FIG. 14 is an explanatory diagram of a change in a display style of classifications in a seventh modification. In the still image 39 illustrated in FIG. 14, an initial H of the character string "Hyper Plastic" used for the first classification 220a is used as a seventh classification 220c. Likewise, an initial A for the character string used for the second classification 222a is used as an eighth classification 222c. An initial H for the character string used for the third classification 224a is used as a ninth classification 224c.

According to the seventh modification, as the style for reducing visual recognizability of a classification, a style for changing text information representing the classification to an initial of the text information may be used. Consequently, visual recognizability of the classification may be reduced and a situation may be avoided in which the classification hinders observation performed by an observer. In addition, the use of both the emphasis display and the classification is enabled.

Eighth Modification

The display of a region of interest may be set in an OFF state in a case where the display style of the region of interest is changed. The display of a classification may be set in an OFF state in a case where the display style of the classification is changed. By using a switch cyclically operated, a standard display style, a display style for continuing the display with reduced emphasis, and a display style for setting the display into the OFF state can be switched between.

Ninth Modification

As the medical image, consecutive images obtained by imaging an observation target with respect to a plurality of planes orthogonal to a given direction may be used. Examples of such consecutive images include CT images, MRI images, etc.

Examples of consecutive image display include a style of consecutively displaying a plurality of tomographic images included in CT images in any single direction. Note that CT is an abbreviation for Computed Tomography. Note that MRI is an abbreviation for Magnetic Resonance Imaging. Note that the first to ninth modifications are applicable to a second embodiment described later.

Medical Image Processing Apparatus According to Second Embodiment

Figure 15:
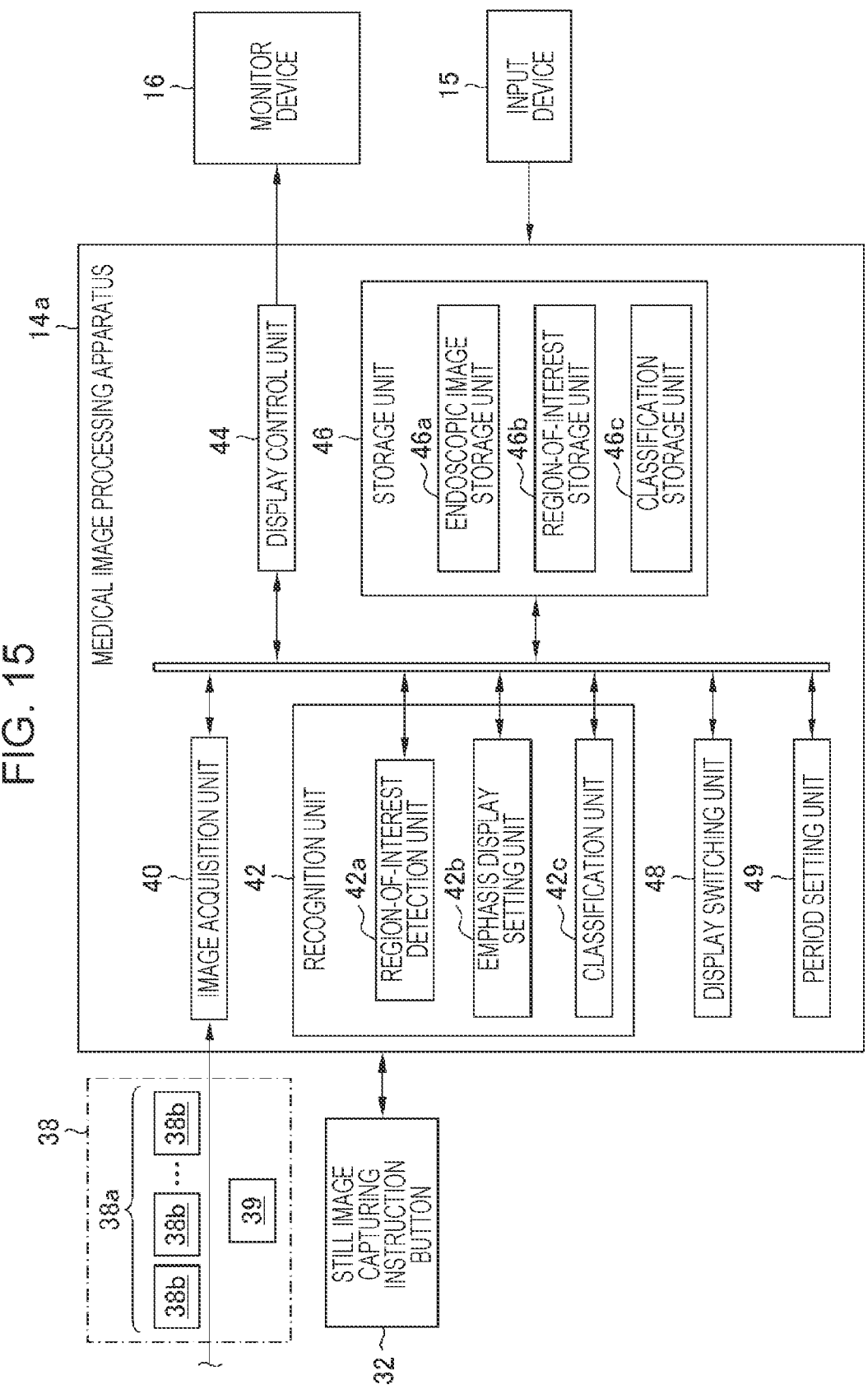
FIG. 15 is a functional block diagram of a medical image processing apparatus according to a second embodiment.

FIG. 15 is a functional block diagram of a medical image processing apparatus according to a second embodiment. A medical image processing apparatus 14a illustrated in FIG. 15 additionally includes a period setting unit 49, compared with the medical image processing apparatus 14 illustrated in FIG. 3.

The period setting unit 49 sets a period from a timing at which display styles of emphasis display and a classification are changed to a timing at which the display styles of the emphasis display and the classification are returned to original display styles set before the change. The period setting unit 49 stores the set period in a predetermined storage unit. The predetermined storage unit may be included in the storage unit 46.

The period setting unit 49 may set the period from the change of the display styles to the return of the display styles on the basis of a signal input from the input device 15. The period setting unit 49 may read out a pre-stored period and set the read-out period as the period from the change of the display styles to the return of the display styles.

As the period setting unit 49, a timer circuit or a counter circuit may be used that starts counting upon a trigger signal and outputs a command signal indicating an elapse of the set period upon an elapse of the set period.

Medical Image Processing Method According to Second Embodiment

Figure 16:
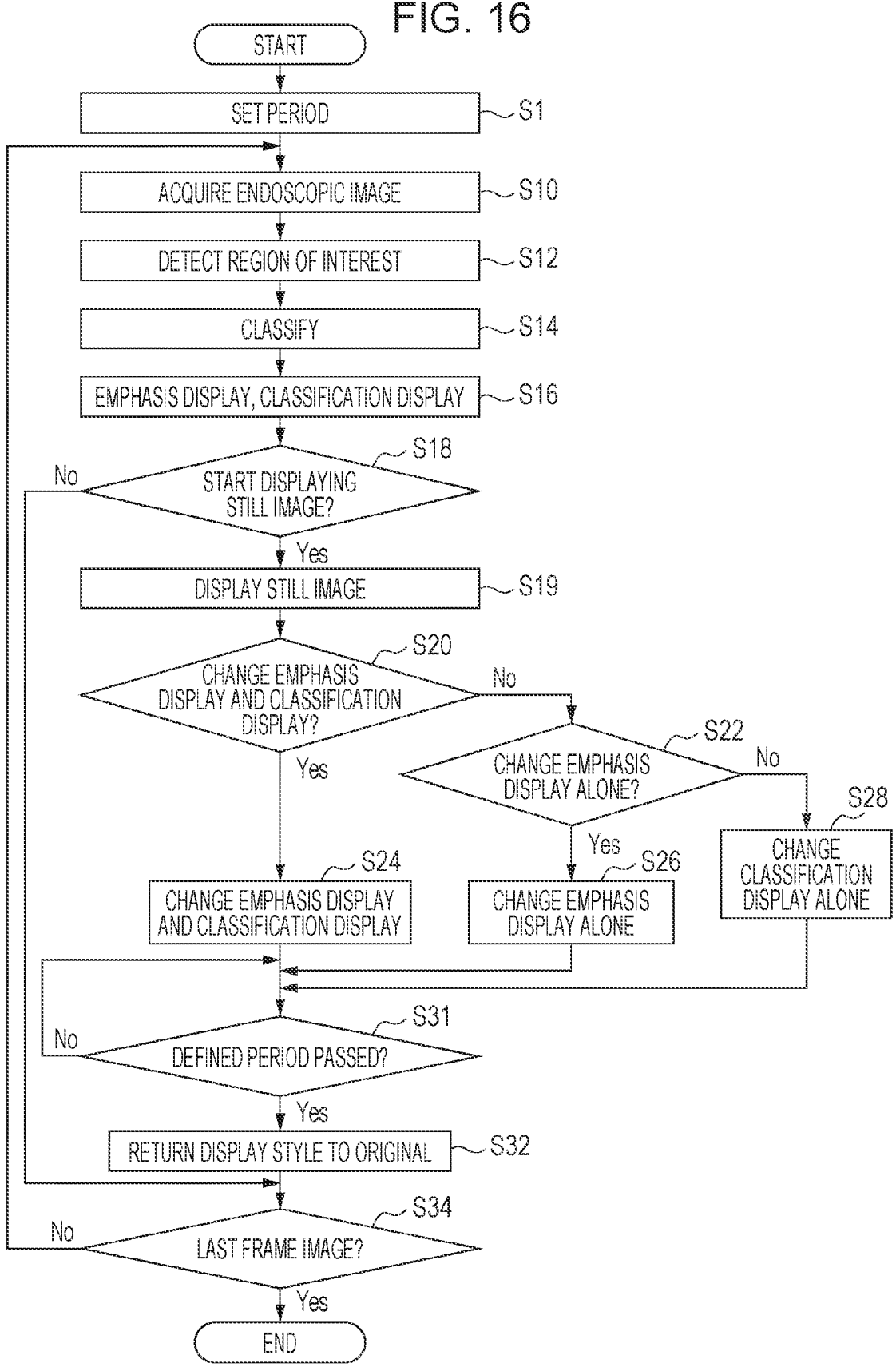
FIG. 16 is a flowchart illustrating a procedure of a medical image processing method according to the second embodiment.

FIG. 16 is a flowchart illustrating a procedure of a medical image processing method according to the second embodiment. The flowchart illustrated in FIG. 16 additionally includes a period setting step S1 and includes an elapse-of-period determining step S31 instead of the whether-to-end-still-image-display determining step S30 illustrated in FIG. 4, compared with the flowchart illustrated in FIG. 4.

In the period setting step S1, the period setting unit 49 sets a period from a timing at which the display styles of emphasis display and a classification are changed to a timing at which the display styles of the emphasis display and the classification are returned to original display styles set before the change.

In the elapse-of-period determining step S31, the display switching unit 48 determines whether the period set in the period setting step S1 has elapsed since the timing at which the display styles are changed. If the display switching unit 48 determines that the set period has not elapsed in the elapse-of-period determining step S31, No is determined. The elapse-of-period determining step S31 is continued until Yes is determined in the elapse-of-period determining step S31.

On the other hand, if the display switching unit 48 determines that the set period has elapsed in the elapse-of-period determining step S31, Yes is determined. The process proceeds to the display return step S32. In the display return step S32, the display switching unit 48 changes the display styles of the emphasis display and the classification to the original display styles.

In the flowchart illustrated in FIG. 16, a setting is made such that the process proceeds to the endoscopic image acquisition step S10 after the period setting step S1. However, it is sufficient that the period setting step S1 is performed before the display styles of the emphasis display and the classification are changed.

Effects of Second Embodiment

With the medical image processing apparatus and the medical image processing method according to the second embodiment, the following effects can be obtained. In addition, the medical image processing apparatus and the like according to the second embodiment can obtain substantially the same effects as those of the first embodiment.

[1]

After a predetermined period has been elapsed since a timing at which display styles of emphasis display and a classification are changed, the display styles of the emphasis display and the classification are returned to original display styles. Consequently, the display styles of the emphasis display and the classification can be automatically returned.

[2]

The predetermined period from the timing at which the display styles of the emphasis display and the classification are changed to the timing at which the display styles of the emphasis display and the classification are returned may be set. Consequently, the period from the change of the display styles to the return of the display styles may be predetermined.

Specific Example of Convolutional Neural Network

Figure 17:
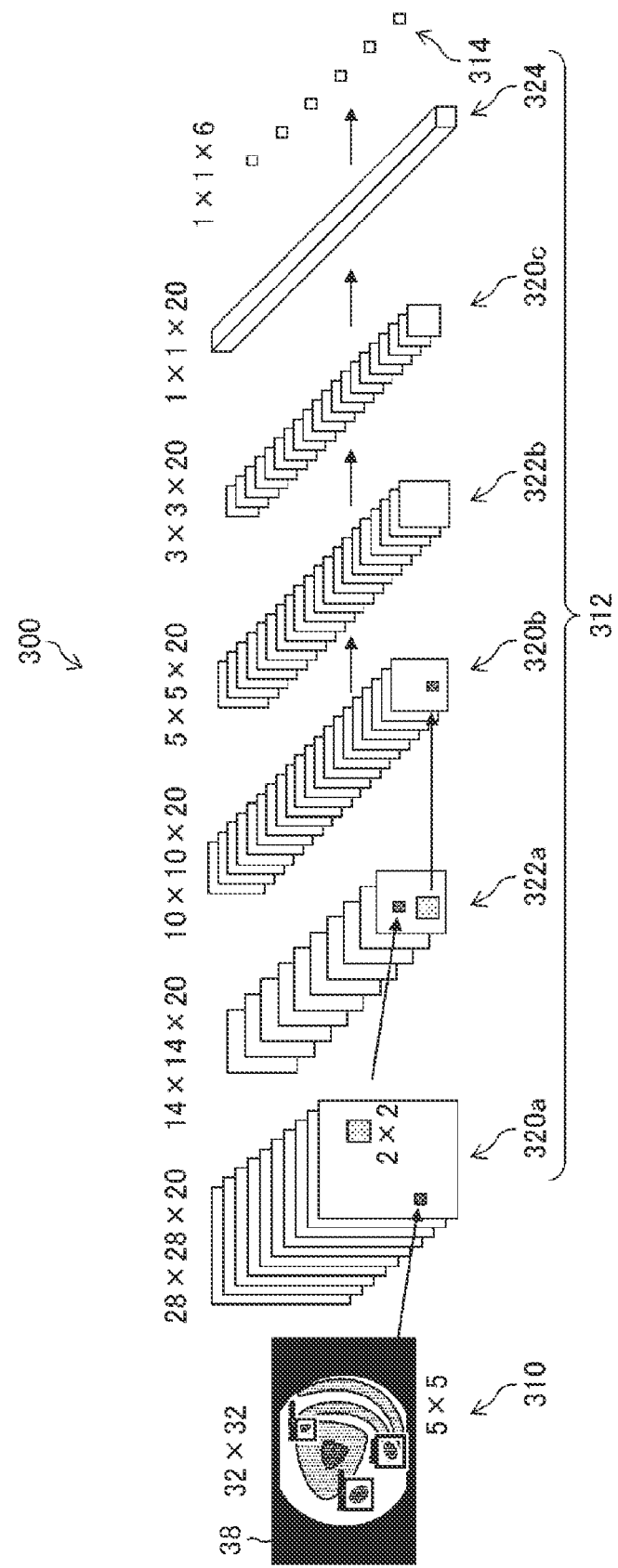
FIG. 17 is an explanatory diagram of a convolutional neural network.

FIG. 17 is an explanatory diagram of a convolutional neural network. A network 300 has a structure constituted by a plurality of layers and holds a plurality of weight parameters. The weight parameters are updated from initial values to optimum values, so that an untrained model becomes a trained model.

The network 300 includes an input layer 310, intermediate layers 312, and an output layer 314. The intermediate layers 312 include a first convolutional layer 320a, a first pooling layer 322a, a second convolutional layer 320b, a second pooling layer 322b, a third convolutional layer 320c, and a fully connected layer 324. Each layer has a structure in which a plurality of nodes are linked to each other by edges.

The endoscopic image 38 to be learned is input to the input layer 310. The intermediate layers 312 extract features from the endoscopic image 38. The first convolutional layer 320a, the second convolutional layer 320b, and the third convolutional layer 320c each perform filtering processing on the nodes in the previous layer to acquire a feature map. That is, the first convolutional layer 320a, the second convolutional layer 320b, and the third convolutional layer 320c each perform a convolutional operation using a filter on the nodes.

The first convolutional layer 320a generates, by using 20 filters, 20 feature maps having a 28×28 size from the endoscopic image 38 having a 32×32 size. The second convolutional layer 320b generates 20 feature maps having a 10×10 size from 20 feature maps having a 14×14 size. The third convolutional layer 320c generates 20 feature maps having a 3×3 size from 20 feature maps having a 5×5 size.

The first pooling layer 322a downsizes the feature maps output from the first convolutional layer 320a to generate new feature maps. The second pooling layer 322b downsizes the feature maps output from the second convolutional layer 320b to generate new feature maps.

The first pooling layer 322a generates the 20 feature maps having the 14×14 size from the 20 feature maps having the 28×28 size. The second pooling layer 322b generates the 20 feature maps having the 5×5 size from the 20 feature maps having the 10×10 size.

The first pooling layer 322a and the second pooling layer 322b play a role of providing the robustness so that the extracted features are not influenced by translation or the like. Note that the intermediate layers 312 are not limited to the case where a convolutional layer and a pooling layer constitute a single set. There may be a case where convolutional layers are consecutive and a configuration including a normalization layer (not illustrated).

The fully connected layer 324 connects all the outputs of the previous layer to all the nodes of the next layer. That is, the fully connected layer 324 connects outputs of the third convolutional layer 320c to all the nodes of the output layer 314.

The output layer 314 outputs features extracted using the intermediate layers 312 from the endoscopic image 38. The recognition unit 42 illustrated in FIG. 3 includes a network that extracts a region of interest from the endoscopic image 38 and a network that classifies the region of interest.

Any initial values are set as filter coefficients and offset values used in the first convolutional layer 320a or the like and as weights of connections in the fully connected layer 324 to the next layer in the network 300 before training.

The network 300 acquires an output result output from the output layer 314 and correct answer data for the output result and calculates an error between the output result and the correct answer data. Examples of the error calculation method include softmax entropy and sigmoid.

The network 300 adjusts the parameters of the network 300 by using error backpropagation on the basis of the calculated error. The network 300 repeatedly adjusts the parameters and performs learning until an error between the output result and the correct answer data becomes small.

The trained network 300 outputs at least any of a region of interest in an input image or a classification for the region of interest. The output result may be used as correct answer data, and the network 300 may be re-trained by using pairs of the input image and the output result.

The network that detects a region of interest from the endoscopic image 38 and the network that classifies the region of interest perform common processing in some of the intermediate layers 312. Accordingly, the network that detects a region of interest from the endoscopic image 38 and the network that classifies the region of interest may use some of the parameters of the intermediate layers 312 in common.

Although illustration is omitted, the recognition unit 42 includes a parameter storage unit that stores parameters used in the network that detects a region of interest from the endoscopic image 38 and parameters used in the network that classifies the region of interest.

The network that detects a region of interest from the endoscopic image 38 and the network that classifies the region of interest may identify the position of the region of interest and classify the region of interest on the basis of an overlapping degree of the feature maps.

The network that detects a region of interest from the endoscopic image 38 and the network that classifies the region of interest may collectively learn detection of a region of interest and classification of the region of interest for a single endoscopic image 38.

The plurality of convolutional layers described in the embodiments correspond to an example of a plurality of downsizing processing units that perform processing for reducing a size of an input image in stages. A combination of the plurality of convolutional layers and the plurality of pooling layers described in the embodiments corresponds to an example of a plurality of downsizing processing units that perform processing for reducing a size of an input image in stages.

The convolutional layer described in the embodiments corresponds to an example of a feature map generation unit that generates a feature map from an output image of each of the plurality of downsizing processing units.

The network 300 described in the embodiments corresponds to an example of a region-of-interest recognition unit that performs at least any of identification of a region of interest or classification of the region of interest from the feature maps.

The pooling layer described in the embodiments corresponds to an example of a pooling processing unit that performs pooling processing on the input image. The convolutional layer described in the embodiments corresponds to an example of a convolutional processing unit.

Modifications of Endoscope System

Modification of Processor Device

The processor device 12 may have the functions of the medical image processing apparatus 14. That is, the processor device 12 and the medical image processing apparatus 14 may be integrated together. In such an embodiment, the display device 13 may also serve as the monitor device 16. The processor device 12 may include a connection terminal to which the input device 15 is connected.

Modifications of Illumination Light

One example of the medical image acquirable by using the endoscope system 9 according to the present embodiments is a normal-light image acquired by radiating light in a white range or light in a plurality of wavelength ranges as the light in the white range.

Another example of the medical image acquirable by using the endoscope system 9 according to the present embodiments is an image acquired by radiating light in a specific wavelength range. A range narrower than the white range may be used as the specific wavelength range. The following modifications may be employed.

First Modification

A first example of the specific wavelength range is a blue range or a green range in a visible range. The wavelength range of the first example includes a wavelength range of 390 nm or more and 450 nm or less or a wavelength range of 530 nm or more and 550 nm or less, and the light of the first example has a peak wavelength in the wavelength range of 390 nm or more and 450 nm or less or the wavelength range of 530 nm or more and 550 nm or less.

Second Modification

A second example of the specific wavelength range is a red range in the visible range. The wavelength range of the second example includes a wavelength range of 585 nm or more and 615 nm or less or a wavelength range of 610 nm or more and 730 nm or less, and the light of the second example has a peak wavelength in the wavelength range of 585 nm or more and 615 nm or less or the wavelength range of 610 nm or more and 730 nm or less.

Third Modification

A third example of the specific wavelength range includes a wavelength range in which an absorption coefficient is different between oxyhemoglobin and deoxyhemoglobin, and the light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or more and 750 nm or less, and the light of the third example has a peak wavelength in the wavelength range of 400±10 nm, the wavelength range of 440±10 nm, the wavelength range of 470±10 nm, or the wavelength range of 600 nm or more and 750 nm or less.

Fourth Modification

A fourth example of the specific wavelength range is a wavelength range of excitation light that is used to observe fluorescence emitted by a fluorescent substance in a living body and excites this fluorescent substance. For example, the specific wavelength range of the fourth example is a wavelength range of 390 nm or more and 470 nm or less. Note that observation of fluorescence may be referred to as fluorescence observation.

Fifth Modification

A fifth example of the specific wavelength range is a wavelength range of infrared light. The wavelength range of this fifth example includes a wavelength range of 790 nm or more and 820 nm or less or a wavelength range of 905 nm or more and 970 nm or less, and the light of the fifth example has a peak wavelength in the wavelength range of 790 nm or more and 820 nm or less or the wavelength range of 905 nm or more and 970 nm or less.

Generation Example of Special-Light Image

The processor device 12 may generate a special-light image having information in the specific wavelength range on the basis of a normal-light image obtained through imaging by using white light. Note that the term "generation" used herein includes "acquisition". In this case, the processor device 12 functions as a special-light image acquisition unit. The processor device 12 obtains a signal of the specific wavelength range by performing calculation based on color information of red, green, and blue or color information of cyan, magenta, and yellow included in the normal-light image.

Note that red, green, and blue are sometimes referred to as RGB. In addition, cyan, magenta, and yellow are sometimes referred to as CMY.

Generation Example of Feature-Quantity Image

As the medical image, a feature-quantity image may be generated by using calculation based on at least any of a normal-light image obtained by radiating light in the white range or light in a plurality of wavelength ranges as the light in the white range or a special-light image obtained by radiating light in the specific wavelength range.

Application Example to Program for Causing Computer to Function as Medical Image Processing Apparatus The above-described medical image processing method can be configured as a program that implements functions corresponding to respective steps of the medical image processing method by using a computer. For example, a program may be configured to cause a computer to implement a recognition function that detects a region of interest from the acquired endoscopic image 38 and classifies the region of interest; a display function that causes emphasis display for emphasizing the region of interest and a classification for the region of interest to be displayed in the same screen as the endoscopic image 38; and an observation image switching function that switches whether to display a moving image of an observation image or to display a still image of the observation image, in which in a case where moving image display of the observation image is switched to still image display by using the observation image switching function, the display function makes a change for reducing visual recognizability of at least any of the emphasis display or the classification compared with a case where the moving image of the observation image is displayed.

A program that causes a computer to implement the above-described image processing functions may be stored on a computer-readable information storage medium which is a non-transitory tangible information storage medium, and the program may be provided using the information storage medium.

In addition, instead of the configuration in which the program is stored on a non-transitory information storage medium and is provided, a configuration in which a program signal is provided via a communication network may be employed.

COMBINATION OF EMBODIMENTS, MODIFICATIONS, ETC

The constituent elements described in the embodiments above and the constituent elements described in the modifications can be appropriately used in combination, and some of the constituent elements can be replaced.

In the embodiments of the present invention described above, the constituent elements can be appropriately changed, added, or deleted within a scope not departing from the gist of the present invention. The present invention is not limited to the embodiments described above, and various modifications can be made by a person having the ordinary skill in the art within the technical sprit of the present invention.

REFERENCE SIGNS LIST 9 endoscope system
10 endoscope
11 light source device
12 processor device
13 display device
14 medical image processing apparatus
14a medical image processing apparatus
15 input device
16 monitor device
20 insertion section
21 operation section
22 universal cord
25 soft part
26 bending part
27 tip part
27a tip surface
28 imaging element
29 bending operation knob
30 air/water supply button
31 suction button
32 still image capturing instruction part
33 treatment tool introduction port
35 light guide
36 signal cable
37a connector 37b connector
38 endoscopic image
38a moving image
38b frame image
39 still image
40 image acquisition unit
42 recognition unit
42a region-of-interest detection unit
42b emphasis display setting unit
42c classification unit
44 display control unit
46 storage unit
46a endoscopic image storage unit
46b region-of-interest storage unit
46c classification storage unit
48 display switching unit
49 period setting unit
120 processor
122 memory
124 storage device
126 network controller
128 power supply device
130 display controller
132 input/output interface
134 input controller
136 bus
140 communication network
200 lesion
200a first lesion
201a first region of interest
202a second lesion
203a second region of interest
204a third lesion
205a third region of interest
210 bounding box
210a first bounding box
210b fourth bounding box
210c seventh bounding box
212 bounding box
212a second bounding box
212b fifth bounding box
212c eighth bounding box
214 bounding box
214a third bounding box
214b sixth bounding box
214c ninth bounding box
220 classification
220a first classification
220b fourth classification
220c seventh classification
222a second classification
222b fifth classification
222c eighth classification
224a third classification
224b sixth classification
224c ninth classification
300 network
310 input layer
312 intermediate layer
314 output layer
320a first convolutional layer
320b second convolutional layer
320c third convolutional layer
322a first pooling layer
322b second pooling layer
324 fully connected layer
S1 to S34 steps of medical image processing method

What is claimed is:

1. A medical image processing apparatus comprising one or more processors configured to:
   detect a region of interest from an acquired medical image and classify the detected region of interest;
   cause emphasis display for emphasizing the region of interest and a classification for the region of interest to be displayed in a screen identical to a screen for displaying an observation target included in the medical image;
   switch whether to display consecutive images of an observation image or to display a still image of the observation image on a display; and
   in a case where switching consecutive image display of the observation image to still image display, make a change for reducing visual recognizability of at least any of the emphasis display or the classification compared with a case of the consecutive image display of the observation image.

2. The medical image processing apparatus according to claim 1, wherein the one or more processors are configured to display the classification in a case where making the change for reducing the visual recognizability of at least any of the emphasis display or the classification compared with the case of the consecutive image display of the observation image.

3. The medical image processing apparatus according to claim 1, wherein the one or more processors are configured to move a position of at least any of the emphasis display or the classification to a position outside a region where the observation image is displayed in the screen where the observation image is displayed.

4. The medical image processing apparatus according to claim 1, wherein the one or more processors are further configured to:
   set a period from a timing at which a display style of at least any of the emphasis display or the classification is changed to a timing at which the display style is returned to an original; and
   return the display style to the original in response to an elapse of the set period since the timing at which the display style of at least any of the emphasis display or the classification is changed.

5. The medical image processing apparatus according to claim 1, wherein the one or more processors are further configured to:
   acquire a command signal transmitted in a case where an operation section is operated; and
   in a case where acquiring a command signal indicating that the consecutive image display of the observation image is to be switched to the still image display, make the change for reducing the visual recognizability of at least any of the emphasis display or the classification compared with the case of the consecutive image display of the observation image.

6. The medical image processing apparatus according to claim 1, wherein the one or more processors are configured to:
   perform processing for reducing a size of an input image in stages to output reduced images; and
   generate a feature map from each of the reduced images.

7. The medical image processing apparatus according to claim 6, wherein the one or more processors are configured to perform at least any of pooling processing on the input image or convolutional processing on the input image.

8. The medical image processing apparatus according to claim 6, wherein the one or more processors are configured to:
generate a plurality of feature maps from the reduced images; and
perform at least any of identification of the region of interest or classification of the region of interest from the generated feature maps.

9. The medical image processing apparatus according to claim 8, wherein the one or more processors are configured to perform detection of the region of interest and classification of the region of interest on the basis of an overlapping degree of the generated feature maps.

10. The medical image processing apparatus according to claim 1, further comprising a parameter storage configured to store parameters obtained by collectively learning detection of a region of interest and classification of the region of interest for at least one image.

11. The medical image processing apparatus according to claim 1, wherein the one or more processors are configured to use, as the emphasis display, a closed curve that surrounds the region of interest, and in a case where changing a display style of the emphasis display, change at least any of a color, a density, or a type of a line of the closed curve.

12. The medical image processing apparatus according to claim 1, wherein the one or more processors are configured to, in a case where changing a display style of the emphasis display, move the emphasis display to a position where visual recognizability of the emphasis display is reduced.

13. The medical image processing apparatus according to claim 1, wherein the one or more processors are configured to use text information representing content of the classification as classification information representing the classification for the region of interest, and in a case where changing a display style of the classification for the region of interest, move the text information to a position where visual recognizability of the text information is reduced.

14. The medical image processing apparatus according to claim 13, wherein the one or more processors are configured to, in a case where changing the display style of the classification for the region of interest, move the text information to a position outside a display region of an image representing the observation target.

15. The medical image processing apparatus according to claim 14, wherein the one or more processors are configured to, in a case where a plurality of regions of interest are detected, move a plurality of pieces of the text information representing classifications for the plurality of regions of interest to a position outside the display region of the image representing the observation target while maintaining a positional relationship among the plurality of regions of interest.

16. The medical image processing apparatus according to claim 13, wherein the one or more processors are configured to, in a case where changing the display style of the classification for the region of interest, cause only an initial of a character string representing a meaning of the classification to be displayed as the text information.

17. The medical image processing apparatus according to claim 1, wherein the one or more processors are further configured to:
control an endoscope; and
detect the region of interest from the medical image, which is acquired by using the endoscope, and classify the detected region of interest.

18. An endoscope system comprising:
an endoscope;
one or more processors configured to control the endoscope; and
the medical image processing apparatus according to claim 1,
wherein the medical image processing apparatus performs processing on an endoscopic image acquired by using the endoscope.

19. A medical image processing method comprising:
detecting a region of interest from an acquired medical image and classifying the region of interest;
causing emphasis display for emphasizing the region of interest and a classification for the region of interest to be displayed in a screen identical to a screen for displaying an observation target included in the medical image;
switching whether to display consecutive images of an observation image or to display a still image of the observation image on a display; and
in a case where switching consecutive image display of the observation image to still image display, making a change for reducing visual recognizability of at least any of the emphasis display or the classification compared with a case of the consecutive image display of the observation image.

20. A non-transitory computer readable recording medium storing a program for causing a computer to implement:
a recognition function that detects a region of interest from an acquired medical image and classifies the region of interest;
a display function that causes emphasis display for emphasizing the region of interest and a classification for the region of interest to be displayed in a screen identical to a screen for displaying an observation target included in the medical image; and
an observation image switching function that switches whether to display consecutive images of an observation image or to display a still image of the observation image on a display device,
wherein in a case where the observation image switching function switches consecutive image display of the observation image to still image display, the display function makes a change for reducing visual recognizability of at least any of the emphasis display or the classification compared with a case of the consecutive image display of the observation image.

* * * * *